(12) United States Patent
Ramakrishnan et al.

(10) Patent No.: US 8,598,137 B2
(45) Date of Patent: Dec. 3, 2013

(54) USE OF SAM68 FOR MODULATING SIGNALING THROUGH THE TNF RECEPTOR

(75) Inventors: Parameswaran Ramakrishnan, Pasadena, CA (US); David Baltimore, Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 27 days.

(21) Appl. No.: 13/284,792

(22) Filed: Oct. 28, 2011

(65) Prior Publication Data

US 2012/0121608 A1 May 17, 2012

Related U.S. Application Data

(60) Provisional application No. 61/408,371, filed on Oct. 29, 2010.

(51) Int. Cl.
*C12N 15/113* (2010.01)
*A61K 39/395* (2006.01)
*C07H 21/04* (2006.01)

(52) U.S. Cl.
USPC ................ 514/44 A; 424/130.1; 536/24.5

(58) Field of Classification Search
None
See application file for complete search history.

(56) References Cited

U.S. PATENT DOCUMENTS

2007/0031410 A1    2/2007  Harton et al.

FOREIGN PATENT DOCUMENTS

WO     WO 2006-017211     2/2006

OTHER PUBLICATIONS

Alvarez et al., Sphingosine-1-phosphate is a missing cofactor for the E3 ubiquitin ligase TRAF2, Nature, Jun. 24, 2010, vol. 465, pp. 1084-1088.
Andera, L., Signaling activated by the death receptors of the TNFR family. Biomedical papers of the Medical Faculty of the University Palacky, Olomouc, Czechoslovakia 153, 173-180, 2009.
Baker et al., Modulation of life and death by the TNF receptor superfamily, Oncogene, 1998, vol. 17, Issue 25, pp. 3261-3270.
Bianchi, K., et al., "A tangled web of ubiquitin chains: breaking news in TNF-R1 signaling." Mol Cell 36, 736-742, 2009.
Bhoj, V.G., and Chen Z.J., Ubiquitylation in innate and adaptive immunity. Nature 458, 430-437, 2009.
Bielli et al. The RNA-binding protein Sam68 is a multifunctional player in human cancer. Endocrine-Related Cancer (2011) 18 R91-R102.
Brenner et al., Mitochondrial cell death effectors, Current Opinion in Cell Biology, Dec. 2009, vol. 21, Issue 6.

Byun, H.S. et al., "Phorbol 12-Myristate 13-Acetate protects against tumor necrosis factor (TNF)-induced necrotic cell death by modulation the recruitment of TNF receptor 1-associated death domain and receptor interating protein I into the TNF receptor 1 signaling complex: Implication for the regulatory erole of protein kinase C", Molecular Pharmacology, 23 Jun. 23, vol. 70, No. 3, 9pp. 1099-1108. See p. 1100 right col. lines 9-16. p. 1101 right column.
Chen et al., TNF-R1 signaling: A beautiful pathway, Science, May 31, 2002, vol. 296, Issue 5573.
Chen et al., Beyond tumor necrosis factor receptor: TRADD signaling in toll-like receptors. Proceedings of the National Academy of Sciences of the United States of America 105, 12429-12434, 2008.
Devin et al, The distinct roles of TRAF2 and RIP in IKK activation by TNF-R1 TRAF2 recruits IKK to TNF-R1 while RIP mediates IKK activation. Immunity 12, 419-429, 2000.
Devin et al., The Role of the death-domain kinase RIP in tumour-necrosis factor induced activation of mitogen-activated protein kinases. EMBO reports 4, 623-627, 2003.
Devin et al, The alpha and beta subunits of IkappaBkinase (IKK) mediate TRAF2-dependent IKK recruitment to tumor necrosis factor (TNF) receptor 1 in response to TNF. Mol Cell Biol 21, 3986-3994, 2001.
Dumont et al., Hydrogen peroxide-induced apoptosis is CD95-independent, requires the release of mitochondria-derived reactive oxygen species and the activation of NF-kB, Oncogene, Jan. 21, 1999, vol. 18, Issue 3, pp. 747-757.
Ea et al., Activation of IKK by TNFα requires site-specific ubiquitination of RIP1 and polyubiquitin binding by NEMO, Molecular Cell, Apr. 21, 2006, vol. 22, Issue 2, pp. 245-257.
El Mabrouk et al., SAM68: a downstream target of angiotensin II signaling in vascular smooth muscle cells in genetic hypertension, American Journal of Physiology—Heart and Circulatory Physiology, May 2004, vol. 286, Issue 5, pp. H1954-H1962.
Ellis et al., Phosphorylation of GAP and GAP-associated proteins by transforming and mitogenic tyrosine kinases, Nature, Jan. 25, 1990, vol. 343, pp. 377-381.
Fusaki et al. Interaction between Sam68 and Src family tyrosine kinases, Fyn and Lck, in T cell receptor signaling. The Journal of biological chemistry 272, 6214-6219, 1997.
Ghosh et al., NF-kB and REL proteins: Evolutionary conserved mediators of immune responses, Annual Review of Immunology, Apr. 1998, vol. 16, pp. 225-260.
Haas, et al. Recruitment of the linear ubiquitin chain assembly complex stabilizes the TNF-R1 signaling complex and is required for TNF-mediated gene induction. Mol Cell 36, 831-844, 2009.
Hao et al. The stability of mRNA influences the temporal order of the induction of genes encoding inflammatory molecules. Nature immunology 10, 281-288.
Hayden et al., Shared principles in NF-kB signaling, Cell, Feb. 8, 2008, vol. 132, Issue 3, pp. 344-362.
He, K.L., et al., "A20 inhibits tumor necrosis factor (TNF) alpha-induced APOPtosis by disrupting recruitment of TRADD and RIP to the TNF receptor 1 complex in Jurkat T cells", Molecular and cellular biology, Sep. 30, 2002, vol. 22 No. 17, pp. 6034-6045.

(Continued)

*Primary Examiner* — Tracy Vivlemore
(74) *Attorney, Agent, or Firm* — Knobbe, Martens, Olson & Bear, LLP

(57) ABSTRACT

Sam68 plays a role in TNF-dependent signaling, including NF-kB signaling and extrinsic activation of apoptosis. In some embodiments, inhibitors of Sam68 are administered to inhibit TNF-dependent signaling, for example to inhibit NF-kB signaling or apoptosis in a patient in need. In some embodiments, functional Sam68 is administered to increase TNF-dependent signaling, for example to induce apoptosis in a patient in need. In some embodiments, methods are provided determining whether the TNF-dependent or TNF-independent branch of a signaling pathway is active in a cell or cells, or for drug screening applications.

20 Claims, 15 Drawing Sheets

(56) References Cited

OTHER PUBLICATIONS

Hildt et al. Identification of Grb2 as a novel binding partner of tumor necrosis factor (TNF) receptor 1. The Journal of experimental medicine 189, 1707-1714, 1999.

Hsu, et al. TNF-dependent recruitment of the protein kinase RIP to the TNF recptor-1 signaling complex. Immunity 4, 387-396, 1996.

Huot et al. An adaptor role for cytoplasmic Sam68 in modulating Src activity during cell polarization. Mol Cell Biol 29, 1993-1943.

Ihnatko et al. TNF signaling: early events and phosphorylation. General physiology and biophysics 26, 159-167, 2007.

International Search Report dated Oct. 28, 2011 received in International Application No. PCT/US201/58468.

Jiang et al. Prevention of constitutive TNF receptor 1 signaling by silencer of death domains. Science (new York, NY 283,543-546, 1999.

Kanayama et al., TAB2 and TAB3 activate the NF-kappaB pathway through binding to polyubiquitin chains. Mol Cell 15, 535-548, 2004.

Karin et al., TNFR signaling: ubiquitin-conjugated TRAFfic signals control stop-and-go for MAPK signaling complexes, Immunological Reviews, Mar. 2009, vol. 228, Issue 1, pp. 225-240.

Kelliher et al., The death domain kinase RIP mediates the TNF-induced NF-kappaB signal. Immunity 8, 297-303, 1998.

Krammer, Review article CD95's deadly mission in the immune system, Nature, Oct. 12, 2000, vol. 407, pp. 789-795.

Kreuz et al., NF-kB inducers upregulate cFLIP, a cycloheximide-sensitive inhibitor of death receptor signaling, Molecular and Cellular Biology, Jun. 2001, vol. 21, Issue 12, pp. 3964-3973.

Lee et al., The kinase activity of Rip1 is not required for tumor necrosis factor-α-induced IkB kinase or p38 MAP kinase activation or for the ubiquitination of Rip1 by Traf2, The Journal of Biological Chemistry, Aug. 6, 2004, vol. 279, pp. 33185-33191.

Li et al., Ubiquitination of RIP is required for tumor necrosis factor alpha-induced NF-kappaB activation. The Journal of biological chemistry 281, 13636-13643, 2006.

Locksley et al., The TNF and TNF receptor superfamilies: integrating mammalian biology, Cell, 2001, vol. 104, Issue 4, pp. 487-501.

Lukong et al., Sam68, the KH domain-containing superSTAR, Biochimica et Biophysica Acta (BBA)—Reviews on Cancer, Dec. 5, 2003, vol. 1653, Issue 2.

Mabrouk et al. SAM68: a downstream target of angiotensin II signaling in vascular smooth muscle cells in genetic hypertension. Multidisciplinary Research Group on Hypertension. American Journal of Physiology—Heart and Circulatory Physiology. Published online before print Dec. 2003, doi 10.1152/ajpheart.00134.2003. AJP—Heart May 2004 vol. 286 No. 5 H1954-H1962. Submitted Jan. 26, 2003; accepted in final form Dec. 19, 203.

Micheau et al., Inductio of TNF receptor I-mediated apoptosis via two sequential signaling complexes, Cell, Jul. 25, 2003, vol. 114, Issue 2.

Mizumoto et al., Programmed cell death (apoptosis) of mouse fibroblasts is induced by the topoisomerase II inhibitor etoposide. Molecular pharmacology 46, 890-895, 1994.

Najib et al., Role of Sam68 as an adaptor protein in signal transduction. Cell Mol Life Sci 62, 36-43, 2005.

Newton et al., Ubiquitin chain editing revealed by polyubiquitin linkage-specific antibodies. Cell 134, 668-678 2008.

O'Donnell et al., Ubiquitination of RIP1 regulates an NF-kappaB-independent cell-death switch in TNF signaling. Curr Biol 17, 418-424 2007.

Pahl, H.L., Activators and target genes of Rel/NF-kappaB transcription factors, Oncogene, 1999, vol. 18, Issue 49, pp. 6853-6866.

Park et al., The death domain superfamily in intracellular signaling of apoptosis and inflammation, Annual Review of Immunology, Jul. 15, 2010, vol. 25, pp. 561-586.

Rahighi et al., Specific recognition of linear ubiquitin chains by NEMO is important for NF-kappaB activation. Cell 136, 1098-1109, 2009.

Ramakrishnan, et al. Receptor-specific signaling for both the alternative and the canonical NF-kappaB activation pathways by NF-kappaB-inducing kinase. Immunity 21, 477-489, 2004.

Ramakrishnan et al., Sam68 is required for both NF-kB activation and apoptosis signaling by the TNF receptor, Molecular Cell, Jul. 22, 2011, vol. 43, pp. 167-179.

Ramakrishnan et al. Sam68 is Required for Both NF-kB Activation and Apoptosis Signaling by the TNF Receptor. Jul. 22, 2011 Molecular Cell 43, Supplemental Information, pp. 1-16.

Repetto et al. Neutral red uptake assay for the estimation of cell viability/cytotoxicity. Nature protocols 3, 1125-1131, 2008.

Roos et al., DNA damage-induced cell death by apoptosis, Trends in Molecular Medicine, Sep. 2006, vol. 12, Issue 9, pp. 440-450.

Rothe et al., The TNFR2-TRAF signaling complex contains two novel proteins related to baculoviral inhibitor of apoptosis proteins. Cell 83, 1243-1252, 1995.

Sambrook et al., Molecular Cloning: A Laboratory Manual, Second Edition (Cold Spring Harbor, NY: Cold Spring Harbor Laboratory Press, 1989) Table of Contents.

Shikama et al., Caspase-8 and caspase-10 activate NF-kappaB through RIP, NIK, and IKKalpha kinases. European journal of immunology, 33, 1998-2006, 2003.

Shu et al., The tumor necrosis factor receptor 2 signal transducers TRAF2 and C-IAP1 are components of the tumor necrosis factor receptor 1 signaling complex. Proceedings of the National Academy of Sciences of the United States of America 93, 13973-13978, 1996.

Song et al. Sam68 up-regulation correlates with, and its down-regulation inhibits, proliferation and tumourigenicity of breast cancer cells. Nov. 2010; 222(3): 227-37. Copyright© 2010 Pathological Society of Great Britain and Ireland. Published by John Wiles & Sons, Ltd.

Taylor et al., An RNA-binding protein associated with Src through its SH2 and SH3 domains in mitosis, Nature, Apr. 28, 1994, vol. 368, pp. 867-871.

Taylor et al., Sam68 experts seperable effects on cell cycle progression and apoptosis. BMC cell biology 5, 5, 2004.

Tokunaga et al., Involvement of linear polyubiquitylation of NEMO in NF-kappaB activation. Nature cell biology 11, 123-132, 2009.

Vallabhapurapu et al., Regulation and function of NF-kB transcription factors in the immune system, Annual Review of Immunology, Apr. 2009, vol. 27, pp. 693-733.

Varfolomeev et al., c-IAP1 and c-IAP2 are critical mediators of tumor necrosis factor alpha (TNFalpha)-induced NF-kappaB activation. The Journal of biological chemistry 283, 24295-24299, 2008.

Varfolomeev et al., Targeted disruption of the mouse Caspase 8 gene ablates cell death induction by the TNF receptors, Fas/Apo1, and DR3 and is lethal prenatally, Immunity, Aug. 1, 1998, vol. 9, Issue 2, pp. 267-276.

Ventura et al., c-Jun NH(2)-terminal kinase is essential for the regulation of AP-1 by tumor necrosis factor. Mol Cell boil 23, 2871-2882 2003.

Vestrepen et al., TLR-4, IL-1R and TNF-R signaling to NF-kappaB: variations on a common theme. Cell Mol Life Sci 65, 2964-2978, 2008.

Vince et al., TRAF2 must bind to cellular inhibitors of apoptosis for tumor necrosis factor (tnf) to efficiently activate nf-{kappa} b and to prevent tnf-induced apoptosis. The Journal of biological chemistry 284, 35906-35915, 2009.

Wajant et al., Tumor necrosis factor signaling, Cell Death and Differentiation, 2003, vol. 10, pp. 45-65.

Wallach et al., Tumor necrosis factor receptor and Fas signaling mechanisms, Annual Review of Immunology, Apr. 1999, vol. 17, pp. 331-367.

Wang et al., Sam68 up-regulation correlates with, and its down-regulation inhibits, proliferation and tumourigenicity of breast cancer cells, J. Pathol, Nov. 2010, vol. 222, Issue 3, pp. 223-226.

Wang et al., TNF-α induces two distinct caspase-8 activation pathways, Cell, May 16, 2008, vol. 133, Issue 4, pp. 693-703.

Wertz et al, De-ubiquitination and ubiquitin ligase domains of A20 downregulate NF-kappaB signalling. Nature 430, 694-699, 2004.

Wu et al., Sensing of Lys 63-linked polyubiquitination by NEMO is a key event in NF-kappaB activation [corrected]. Nature cell biology 8, 398-406, 2006.

(56) References Cited

OTHER PUBLICATIONS

Yamazaki et al., Two mechanistically and temporally distince Nf-kappaB activation pathways in IL-1 signaling. Science signaling 2, ra66, 2009.

Yeh et al., Early lethality, functional NF-kappaB activation, and increased sensitivity to TNF-induced cell death in TRAF2-deficient mice. Immunity 7, 715-725.

Zhang et al., Recruitment of the IKK signalosome to the p55 TNF receptor: RIP and A20 bind to NEMO (IKKgamma) upon receptor stimulation. Immunity 12, 301-311, 2000.

A

B

C

D

A shRNA: Control    Sam68

68kDa — Sam68
43kDa — Actin

B siRNA: Control  Sam68

68kDa — Sam68
43kDa — Actin

C

Relative expression

TNF-α

TNF min:  0  30  180   0   30  180
siRNA:     Control        Sam68

USE OF SAM68 FOR MODULATING SIGNALING THROUGH THE TNF RECEPTOR

CROSS-REFERENCE TO RELATED APPLICATIONS

This application claims the benefit of U.S. Provisional Application 61/408,371, filed on Oct. 29, 2010, which is incorporated herein by reference in its entirety.

STATEMENT REGARDING FEDERALLY SPONSORED R&D

This invention was made with government support under GM039458 awarded by the National Institutes of Health. The government has certain rights in the invention.

REFERENCE TO SEQUENCE LISTING

The present application is being filed along with a Sequence Listing in electronic format. The Sequence Listing is provided as a file entitled CALTE_077_SEQLIST.TXT, created Oct. 28, 2011, which is 10 kb in size, and updated by the file entitled CALTE077AREPLACEMENT.TXT, created Jan. 27, 2012, which is 8.5 kb in size. The information in the electronic format of the Sequence Listing is incorporated herein by reference in its entirety.

BACKGROUND OF THE INVENTION

1. Field of the Invention

The present application relates generally to monitoring and altering the activity of cellular signaling pathways involving the protein Sam68.

2. Description of the Related Art

Sam68 is also known as KHDRBS1 (KH domain containing, RNA binding, signal-transduction associated 1). Sam68, a specific target of the Src tyrosine kinase in mitosis, is a KH domain containing RNA binding protein that also contains multiple proline rich regions that bind to SH2, SH3 and WW domain containing proteins (Ellis et al., 1990. Nature 343, 377-381) (Taylor and Shalloway, 1994. Nature 368, 867-871) (Lukong and Richard, 2003. Biochimica et biophysica acta 1653, 73-86). Sam68 also contains an RNA binding domain, the GRP33/SAM68/GLD-1 (GSG) domain (Reviewed in Bielli et al., 2011, Endocrine-Related Cancer 18: R91-R102). However, most of Sam68's function has been attributed to its RNA binding property by which it regulates metabolism, nuclear export and stability of RNA. In line with its functional diversity, Sam68 exists both in the cytoplasm as well as the nucleus and undergoes various post-translational modification including phosphorylation, methylation and acetylation, which modulates its function (Lukong and Richard, 2003. Biochimica et biophysica acta 1653, 73-86.). No known roles for Sam68 in cytokine receptor signaling have been reported before.

TNFα is a potent cytokine that plays an important role in inflammatory response, immunity, cell growth and differentiation as well as apoptosis. These biological processes are mediated by TNF binding to the TNF receptor 1 and TNF receptor 2, where the latter acts as a modulator of the signaling through the former in many cell types. The majority of the known functions of TNF occur through TNF receptor 1 triggering, which initiates either a pro-survival pathway, mainly through the activation of the transcription factor NF-κB, or an extrinsic apoptotic pathway through the activation of caspases under conditions where NF-κB activation or de novo protein synthesis is inhibited. In addition, TNF signaling also triggers MAP kinases activating JNK, p38 and ERK pathways, which also contribute to biological effects TNF (Locksley et al., 2001. Cell 104, 487-501) (Wallach et al., 1999. Annual review of immunology 17, 331-367) (Wajant et al., 2003. Cell death and differentiation 10, 45-65).

The NF-κB family of transcription factors is composed of five members: p65 (RelA), RelB, c-Rel, NF-κB1 (which occurs both as a precursor, p105, and in a processed form, p50), and NF-κB2 (which occurs both as a precursor, p100, and as its processed product, p52). Three of them, c-REL, RelB and RelA, have a carboxy-terminal non-homologous transactivation domain that activate transcription from NF-κB binding sites in target genes. In the resting state, NF-κB proteins exist as homo- or hetero-dimers in the cytoplasm bound to the inhibitory proteins of the IκB family. Activation occurs by signal induced phosphorylation, ubiquitylation and proteasomal degradation of the IκB proteins releasing the bound NF-κB proteins, which in turn translocates to the nucleus to initiate transcription (Ghosh et al., 1998). IκB's are phosphorylated by the upstream kinase complex called signalosome, mainly composed of IKK1, IKK2 and NEMO, which are activated following their recruitment to the TNFR (Hayden and Ghosh, 2008. Cell 132, 344-362.) (Vallabhapurapu and Karin, 2009. Annual review of immunology 27, 693-733.)

Apoptosis plays a role in maintenance of tissue homeostasis and development, supporting equilibrium between cellular proliferation and death. While the survival pathway mainly relies on activation of NF-κB (Baker and Reddy, 1998), apoptosis depends on activation of caspases (Varfolomeev et al., 1998. Immunity 9, 267-276.) (Wang et al., 2008. Cell 133, 693-703.). Apoptosis can occur either by an extrinsic pathway or by an intrinsic pathway. In the intrinsic pathway, non-receptor cellular stress like DNA damage or oxidative stress causes increase in mitochondrial permeability, which leads to release of pro-apoptotic factors in to the cytosol that activate caspases (Brenner and Mak, 2009. Current opinion in cell biology 21, 871-877.). In the extrinsic pathway, the apoptosis is initiated by a death inducing ligand binding to its cognate receptor in the membrane followed by recruitment, aggregation and activation of caspases (Park et al., 2007. Annual review of immunology 25, 561-586.). Signaling through TNF can induce apoptosis via the extrinsic pathway. Moreover, Fas is a prototypic death receptor that induce apoptosis by the extrinsic pathway in a TNF-independent manner (Krammer, 2000. Nature 407, 789-795.) (Wallach et al., 1999. Annual review of immunology 17, 331-367.).

SUMMARY OF THE INVENTION

Sam68 participates in TNF-dependent signaling, and inhibition of Sam68 can inhibit one or both of TNF-dependent activation of the NF-kB pathway and the pro-apoptotic pathway. In light of this finding, Sam68 can be used to modulate TNF-dependent signaling and related biological activities.

In one aspect, methods of modulating TNF-dependent cytokine receptor signaling in a cell or population of cells are provided. The methods typically comprise administering an inhibitor of Sam68 to the cell or cells. In some embodiments the cytokine receptor signaling is TNF-dependent NF-kB signaling. In some embodiments the cytokine receptor signaling is TNF-dependent signaling via the extrinsic apoptosis pathway. The Sam68 inhibitor may be, for example, siRNA, shRNA or an anti-Sam68 antibody. At least one marker of TNF-dependent signaling may be monitored in the cell or cells. In some embodiments the marker may be associated with TNF-dependent NF-kB signaling. For example, the marker may be selected from the group consisting of ubiquitylated RIP, association of TRAF2 with TNFR, phosphorylation of IKK1, phosphorylation of IKK2, phosphorylation of NEMO, ubiquitylation of RIP, ubiquitylation of at least one IκB protein, IκBα degradation, translocation of at least one NF-κB family transcription factors into the nucleus, and expression of at least one NF-κB target gene. In other embodiments, the marker may be associated with activation of the extrinsic apoptosis pathway. For example, the marker may be selected from the group consisting of cleaved PARP, cleaved Caspase 3, cleaved Caspase 8 trypan blue exclusion of dead cells, neutral red assay, TUNEL staining, and association of RIP with FADD.

In another aspect, methods of treating a disease or disorder associated with TNF-dependent signaling are provided. A patient may be identified as suffering from a disease or disorder associated with TNF-dependent signaling. TNF-dependent signaling may be inhibited by administering a therapeutically effective amount of Sam68 inhibitor to the patient. The Sam68 inhibitor may be, for example, an siRNA, shRNA or anti-Sam68 antibody. Markers of TNF-dependent signaling may be monitored in the patient. In addition, markers associated with the state and/or progression of the disease or disorder may be monitored.

In another aspect, methods of disrupting a TNF signaling complex in a mammalian cell are provided. In some embodiments a Sam68 inhibitor is administered to a mammalian cell or population of cells and at least one marker of the integrity or activity of a TNF signaling complex is monitored in the cell or cells. The TNF signaling complex may be complex I or complex II. The marker may be, for example, ubiquitylated RIP, association of TRAF2 with TNFR or association of RIP with FADD.

In another aspect, activation of an extrinsic apoptosis pathway in a mammal is increased. Sam68 is provided to one or more cells of the mammal in which increased apoptosis is desired. The cells may be, for example, cells associated with a disease or disorder, such as cancer cells. In some embodiments the cells may be part of a tumor. In some embodiments, a biological sample is obtained from the mammal and at least one marker of apoptotic activation is monitored in the sample. The sample may be obtained before or after providing Sam68 to the cells. In some embodiments, a sample is obtained both before and after providing Sam68 to the cells. Sam68 may be provided to the cells, for example, by contacting the cells with a nucleic acid encoding a functional Sam68 protein. The nucleic acid may, for example, be part of a genetic construct such as an expression vector. In other embodiments Sam68 is provided to the cells by increasing expression of endogenous Sam68 in the target cells. Increasing activation of apoptosis by providing cells with Sam68 may also be used to treat a disease or disorder in some embodiments.

In another aspect, the ability of a compound to act through TNF-dependent signaling may be determined. The compound may be, for example, a candidate therapeutic compound. Compounds may be, for example, small molecules, antibodies or polypeptides. In some embodiments Sam68 is inhibited in one or more cells and the cell or cells are subsequently contacted with the compound. At least one marker of TNF-dependent signaling in the cell or cells is monitored. The TNF-dependent signaling may be NF-kB signaling or signaling via an extrinsic apoptosis pathway. In some embodiments the compounds are tested in a Sam68 knock out cell line. In some embodiments Sam68 activity may be inhibited by contacting the one or more cells with a Sam68 inhibitor, such as an siRNA, shRNA or anti-Sam68 antibody. The ability of the compound to stimulate TNF-dependent signaling in cells in which Sam68 activity has been reduced or eliminated can be compared to the compounds ability to stimulate TNF-dependent signaling in cells in which Sam68 activity has not been intentionally manipulated. Reduction of TNF-dependent signaling in cells in which Sam68 has been inhibited indicates that the compound acts, at least in part, through the TNF-dependent signaling pathway.

Cells were treated with TNF (1 mg/ml) for the indicated times (A). Complex II was immunoprecipitated through FADD and analyzed for the presence of RIP, caspase-8, and Sam68. Bottom panels show RIP levels in the lysate and actin as control. Total lysates in (B) from (A) were immunoblotted using anti-PARP, anti-cleaved caspase-3, caspase-8, and actin antibodies. Cells in (C) were treated as in (A), and Sam68 immunoprecipitates were analyzed for the presence of FADD, caspase-8, and RIP.

Figure 13:
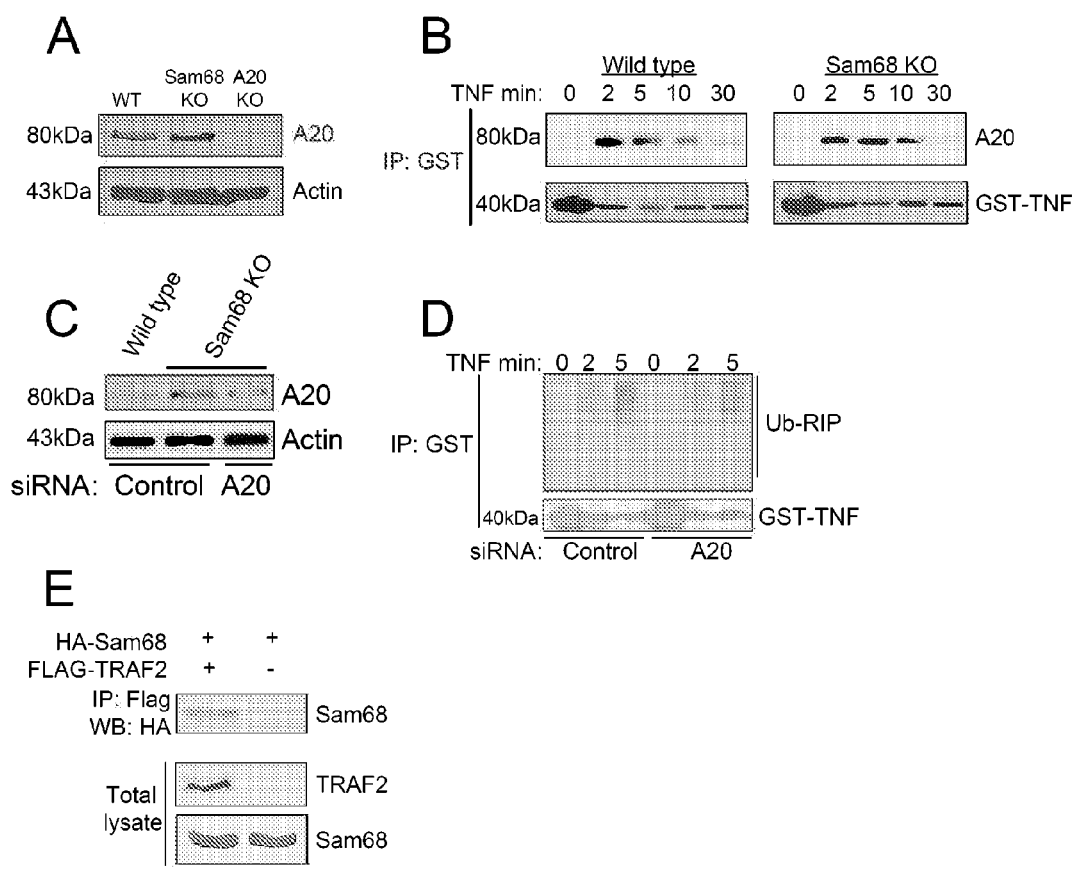

FIG. 13 illustrates Sam68 Deficiency Enhances A20 Level, Yet Not Its Function. (A) Wild type and Sam68 knockout cells were analyzed for A20 expression level. A20 knockout MEF cells were used as negative control. (B) A20 recruitment to TNFR was assessed as in FIG. 7B. (C) siRNA mediated suppression of A20 in Sam68 knockout cells. Cells were transfected with siRNA A20 by nucleofection and 48 hours later total lysates were probed for A20. (D) RIP recruitment to TNFR in control and siRNA A20 transfected Sam68 knockout cells. The precipitated receptor complex was probed for RIP (top panel) and GST-TNF (bottom panel). Sam68 binds to TRAF2. (E) HEK-293T cells were transfected with the indicated plasmids and TRAF2 was immunoprecipitated using anti-FLAG antibody. Binding of HA tagged Sam68 to TRAF2 was detected by immunoblotting using anti-HA antibody (top panel). Bottom panels show the expression of transfected proteins using anti-FLAG and anti-HA antibodies to detect TRAF2 and Sam68 respectively.

Figure 9:
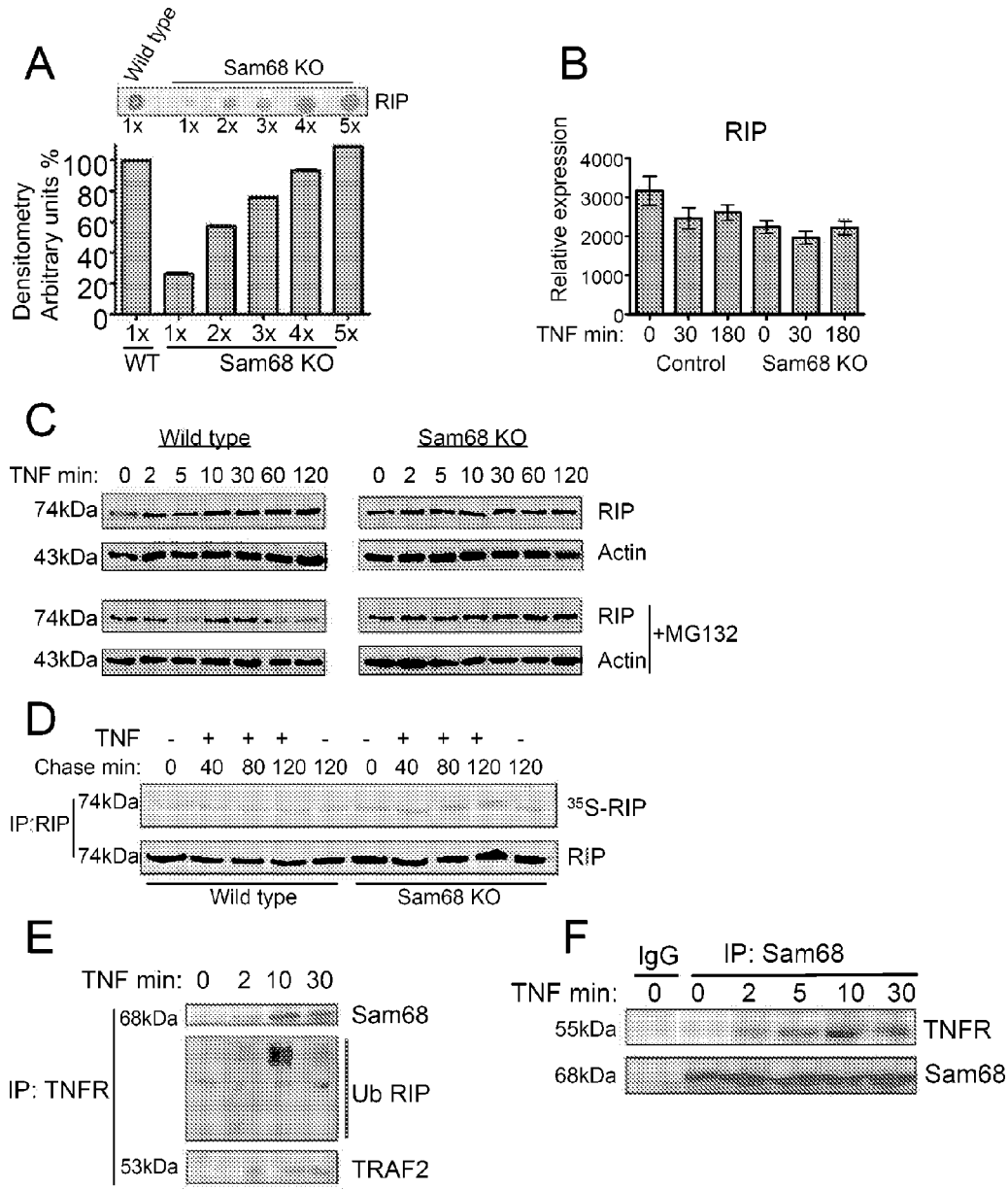
FIG. 9 illustrates Sam68 is recruited to the TNF receptor in HeLa cells. (A) Control and Sam68 knockout cells were treated with GST-TNF for 5 min, TNFR complex was precipitated using glutathione beads, eluted and the eluate from wild type cells was dot blotted at 1× concentration and that from Sam68 knockout cells was dot blotted at various concentrations as indicated and probed using RIP antibody. In the bottom panel RIP levels were evaluated through densitometry (B) RIP expression level in control and Sam68 knockout cells were determined as in FIG. 2. Data are represented as mean+/−SEM. TNFR stimulation does not induce RIP degradation. (C) Cells were treated with the proteasomal inhibitor MG132 (25 μM) for 2 hours and then treated with TNF for the indicated time points. Cells were harvested at 4 hours of incubation with MG132 and total lysates were analyzed for RIP levels. (D) Pulse-chase assay of TNF induced RIP degradation. Immunoprecipitated RIP was analyzed by autoradiography (top panel) and western blotting (bottom panel). Sam68 is recruited to the TNFR. (E) Sam68-TNFR binding in HeLa cells. 20×106 cells were treated with TNF as indicated and TNFR was immunoprecipitated using anti-TNFR antibody. Immunoblotting was performed with Sam68 (top panel), RIP (middle panel) and TRAF2 (bottom panel) antibodies. (F) Reverse immunoprecipitation of TNFR through Sam68. 20×106 wild type MEF cells were treated with TNF as indicated and Sam68 was immunoprecipitated using anti-Sam68 antibody. Co-precipitation of TNFR was detected by immunoblotting using anti-TNFR antibody. Immunoprecipitation using rabbit-IgG was used as a control for non-specific binding. Bottom panel shows amount of Sam68 in the immunoprecipitate.
Figure 14:
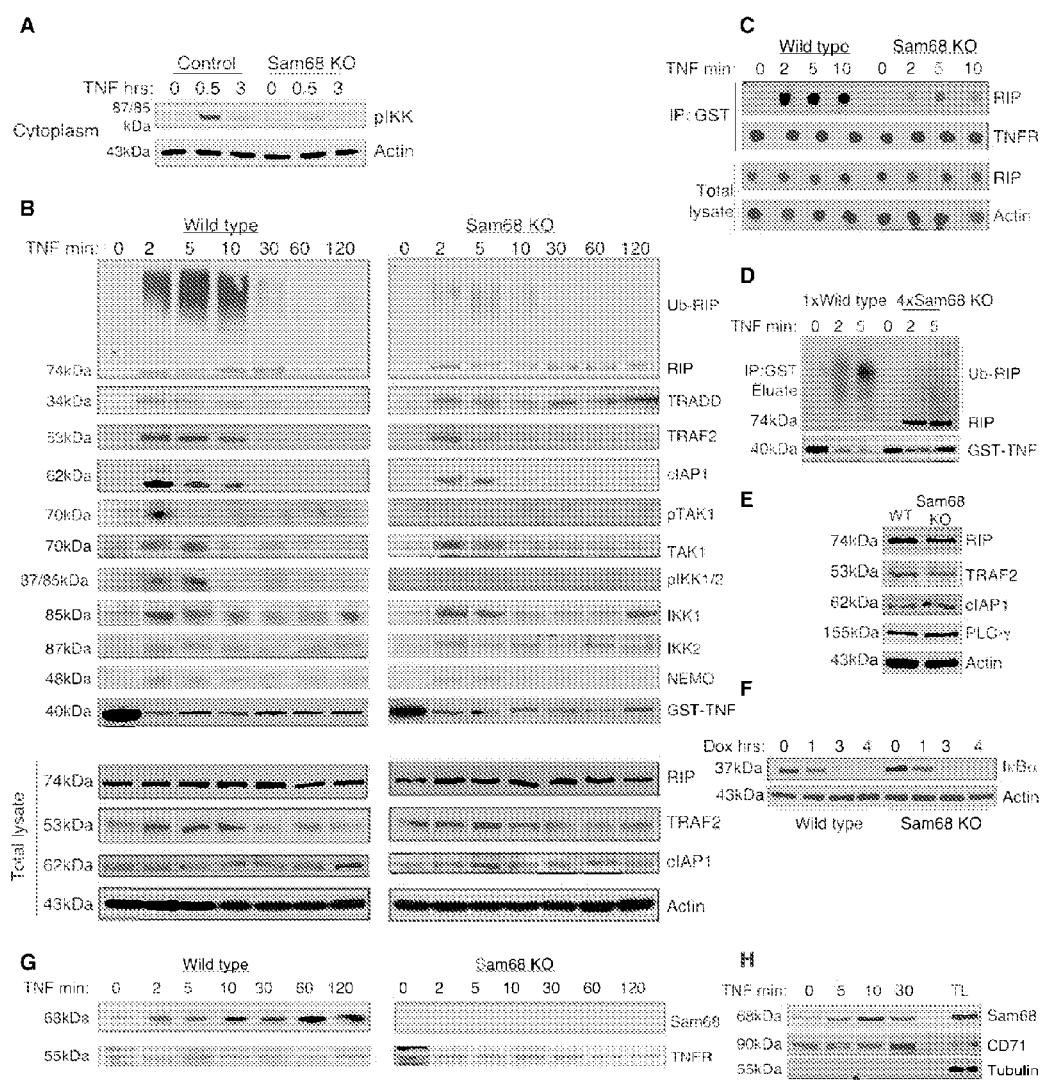

FIG. 14 illustrates that Sam68 Is Required for Signaling from Complex I of TNFR. (A) Cells were treated as in FIG. 1A, and cytoplasmic extracts were immunoblotted with anti-phospho-IKK (pIKK) antibody. (B) Kinetic analysis of recruitment of signaling molecules to TNFR. Cells were treated with GST-TNF for the indicated times, and the receptor-associated complex immunoprecipitated through the GST-tag using glutathione Sepharose beads (top 11 panels) and total lysates (bottom 4 panels) was immunoblotted using the indicated antibodies. The data are representative of seven independent experiments. (C) Eluates from glutathione beads (top panels) and total lysates (bottom panels) were analyzed for total RIP levels by dot blotting. TNFR and actin were used as loading controls. (D) Eluate from glutathione beads approximately normalized for total RIP levels in wild-type and Sam68 knockout cells by loading 4 times the sample from the latter was analyzed by western blotting for RIP and GST-TNF. (E) Total cell lysates from wild-type and Sam68 knockout cells were analyzed for indicated proteins. (F) Cells were treated with 10 mg/ml doxorubicin, and IkBa degradation was studied at indicated times. (G) Cells were treated and immunoprecipitated as above, and Sam68 recruitment was assessed by immunoblotting. TNFR shows the uniformity of immunoprecipitation. See also FIG. 9. (H) Sam68 is present in association with cell membrane. MEF cells were treated with TNF as above, and membrane fractions were immunoblotted with anti-Sam68, anti-CD71, and tubulin antibodies. Total cell lysate was loaded as a control for protein expression. See also FIG. 9.

Figure 15:
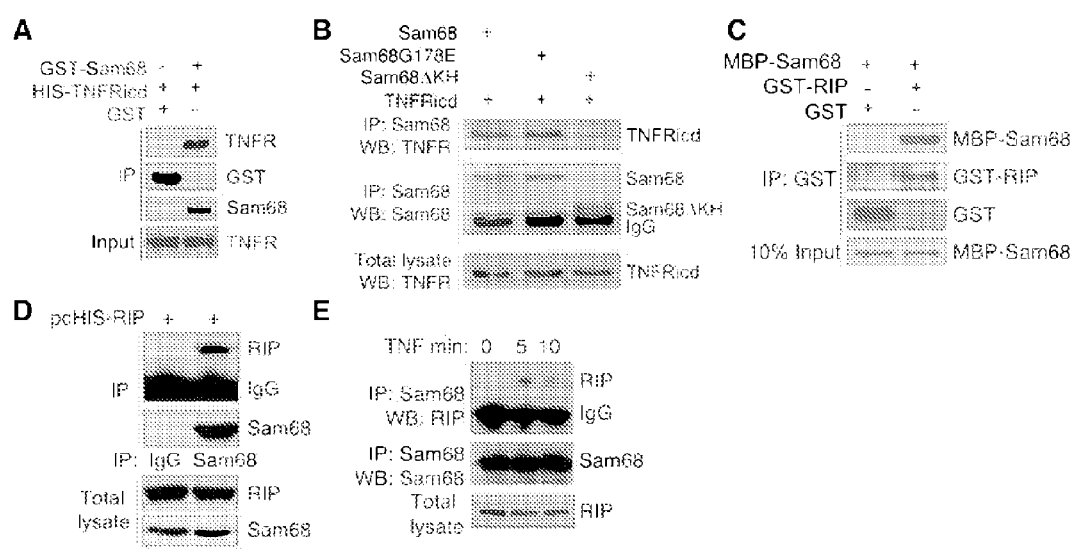

FIG. 15 illustrates that Sam68 Binds to TNFR and RIP. (A and B) KH domain of Sam68 is required for its binding to TNFR. In vitro binding assay of recombinant GST-Sam68 and HIS-TNFRicd is shown (A). HeLashRNA-Sam68 cells were transfected with the indicated plasmids (B). Sam68 immunoprecipitate was probed for TNFRicd (B, top panel) and Sam68 (B, middle panel). The bottom panel shows the expression level of TNFRicd in the cell lysates. (C-E) Sam68 binds to RIP. In vitro binding assay of recombinant MBP-Sam68 to GST-RIP is shown (C). 293T cells were transfected with pcHIS-RIP, and immunoprecipitation was done with anti-Sam68 or rabbit IgG as control (D). MEF cells were treated with TNF for the indicated time points. Sam68 was immunoprecipitated and probed for RIP binding (E).

DETAILED DESCRIPTION OF THE PREFERRED EMBODIMENT

A role for Sam68 has been identified in signaling through the TNF receptor, including TNF-dependent NF-kB signaling and the extrinsic apoptosis pathway. As discussed below, Sam68 can thus be used to modulate signaling through the TNF-dependent signaling pathway. For example, inhibition of Sam68 can be used to block TNF-dependent NF-kB signaling and/or to reduce TNF-dependent apoptotisis. Sam68 can be inhibited, for example, by reducing Sam68 expression or interfering with the function of Sam68, such as by disrupting its role in the formation of Complex I or Complex II. In other embodiments, increasing the amount, expression and/or activity of Sam68 can be used to increase TNF-dependent NF-kB signaling and/or TNF-dependent apoptosis.

Modulation of Sam68 activity can also be used to treat diseases or disorders that are associated with, related to, or involve TNF-dependent NF-kB signaling or TNF-dependent apoptosis. For example, autoimmune type I diabetes can be ameliorated by inhibiting TNF function. Other examples of diseases for which beneficial effects could be obtained by reducing TNF signaling, for example by inhibiting Sam68, are rheumatoid arthritis, Crohn's disease, and a variety of cancers, such as colorectal cancer, melanoma, leukemia, lymphoma, and hepatitis C virus infection induced carcinogenesis. For example, a disease or disorder that involves TNF-dependent NF-kB signaling, such as increased signaling, can be treated by inhibition of Sam68, thereby blocking or reducing TNF-dependent NF-kB signaling. In some embodiments, a patient suffering from inflammation is treated by inhibiting Sam68. On the other hand, a disease or disorder that involves decreased TNF-dependent NF-kB signaling may be treated by increasing the activity and/or amount of Sam68. In some embodiments, the decrease or increase in TNF-dependent NF-kB signaling can be achieved without significantly impacting the other, non-TNF-dependent NF-kB signaling pathways.

In other embodiments, diseases or disorders that might benefit from decreased activity of the extrinsic apoptosis pathway may be treated by inhibition of Sam68. For example, the amount or activity of Sam68 may be reduced. On the other hand, in patients suffering from diseases in which extrinsic apoptosis is defective, for example due to inhibition of Sam68 activity, Sam68 activity can be increased, thereby increasing apoptosis.

Additionally, Sam68 can be used to identify TNF-dependent and TNF-independent signaling in mammalian cells, for example to diagnose a disease state in a patient. Sam68 can also be used to determine whether a compound acts through the TNF-dependent signaling pathway and thus can be used to screen for drug compounds that specifically affect signaling in a TNF-dependent or TNF-independent manner.

DEFINITIONS

As used herein, the terms "inhibitor" and "Sam68 inhibitor" are used in the broadest sense, and refer to any molecule or compound that blocks, inhibits, or reduces, either partially or fully, a biological activity mediated by Sam68. Such activities can include TNF-dependent NF-kB signaling and apoptosis induced through the extrinsic pathway. Sam68 inhibitors may act directly on Sam68 or indirectly, such as by reducing expression of Sam68. Sam68 inhibitors may include, but are not limited to, small organic and inorganic molecules, nucleic acids, peptides, peptide mimetics and antibodies. In some embodiments a Sam68 inhibitor is a nucleic acid molecule that reduces expression of Sam68. For example, a Sam68 inhibitor may be an antisense nucleic acid, an siRNA or an shRNA. In some embodiments a Sam68 inhibitor is a polypeptide, such as an antibody, that prevents Sam68 from performing a normal function in the TNF receptor signaling pathway, or reduces its ability to perform such a function, such as by preventing Sam68 from facilitating formation of Complex I or Complex II. In some embodiments a Sam68 inhibitor may be a molecule that reduces or prevents expression of Sam68. Examples of compositions and methods for inhibiting Sam68 are described below. Inhibition of Sam68 can be accomplished by providing a single Sam68 inhibitor, or by providing a combination of two or more Sam68 inhibitors.

As used herein, the term "treatment" refers to a clinical intervention made in response to a disease, disorder or physiological condition manifested by a patient. In some embodiments the disease, disorder or physiological condition involves TNF receptor signaling, for example through the activation of the transcription factor NF-kB, through activation of the extrinsic apoptosis pathway, or both. The aim of treatment may include, but is not limited to, one or more of the alleviation or prevention of symptoms, slowing or stopping the progression or worsening of a disease, disorder, or condition and the remission of the disease, disorder or condition. In some embodiments, "treatment" refers to both therapeutic treatment and prophylactic or preventative measures. Those in need of treatment include those already affected by a disease or disorder or undesired physiological condition as well as those in which the disease or disorder or undesired physiological condition is to be prevented. For example, in some embodiments treatment may reduce inflammation in a subject, where the inflammation involves TNF-dependent NF-kB signaling.

As used herein, the term "effective amount" or "effective dose" refers to an amount sufficient to effect beneficial or desirable clinical results. An effective amount of Sam68 or of a Sam68 inhibitor is an amount that is effective to treat a disease, disorder or unwanted physiological condition.

As used herein, the term "inhibiting Sam68," and the related terms "inhibit Sam68", "inhibits Sam68" and "inhibition of Sam68" refer to reducing expression levels or activity levels of Sam68, either partially or completely. Examples of inhibiting Sam68 include: completely eliminating expression of Sam68 transcript; reducing, but not eliminating expression of Sam68 transcript; completely eliminating expression of Sam68 protein; reducing, but not eliminating expression of Sam68 protein; completely eliminating Sam68 protein activity; and reducing, but not eliminating Sam68 protein activity. Examples of compositions and methods for inhibiting Sam68 are described below.

The term "antibody" herein is used in the broadest sense and specifically covers human, non-human (e.g. murine) and humanized monoclonal antibodies, including full length monoclonal antibodies, polyclonal antibodies, multi-specific antibodies (e.g., bispecific antibodies), and antibody fragments, so long as they exhibit the desired biological activity.

"Antibody fragments" comprise a portion of a full-length antibody, generally the antigen binding or variable domain thereof. Examples of antibody fragments include Fab, Fab', F(ab')2, and Fv fragments; diabodies; intrabodies; linear antibodies; single-chain antibody molecules; and multi-specific antibodies formed from antibody fragments.

The term "monoclonal antibody" as used herein refers to an antibody obtained from a population of antibodies wherein the individual antibodies comprising the population are identical except for possible naturally occurring mutations that may be present in minor amounts. Monoclonal antibodies are highly specific and are directed against a single antigenic site. In addition, monoclonal antibodies may be made by any method known in the art.

Compositions and Methods for Inhibiting Sam68:

In some embodiments, methods of inhibiting Sam68 are provided. In some embodiments, inhibiting Sam68 is accomplished by administering an inhibitor of Sam68 to a cell, population of cells, tissues or organism. The cell, population of cells, tissue or organism is one in which reduction of TNF-dependent signaling is desired, such as TNF-dependent NF-kB signaling and/or TNF-dependent apoptosis. A Sam68 inhibitor may be administered in vitro in some embodiments. In other embodiments a Sam68 inhibitor may be administered in vivo or ex vivo.

TNF-dependent signaling may be measured before or after administering the Sam68 inhibitor. In some embodiments TNF-dependent signaling is measured both before and after administering the Sam68 inhibitor. In some embodiments, Sam68 activity is completely eliminated. In some embodiments, Sam68 activity is reduced, but not eliminated. In some embodiments, Sam68 expression is completely eliminated. In some embodiments, Sam68 expression is reduced, but not eliminated.

In some embodiments, a Sam68 inhibitor dosage is provided which substantially reduces TNF-dependent signaling with a less substantial effect on other Sam68 activities.

In some embodiments, Sam68 activity is inhibited by preventing or reducing expression of the Sam68 gene product. In some embodiments, Sam68 transcript, including pre-mRNA and mRNA is degraded. In some embodiments, the Sam68 transcript in degraded through the RNA interference (RNAi) pathway. In some embodiments, antisense polynucleotides are targeted against the Sam68 transcript. In some embodiments, Sam68 is inhibited by Sam68 decoy RNAs. Sam 68 decoy RNAs are short RNA molecules that competitively bind to RNA binding proteins or RNA particles that positively regulate full-length Sam68 mRNA, thereby reducing the rate of translation of Sam68. In some embodiments, Sam68 activity is inhibited by impairing the function of or by degrading the Sam68 protein. In some embodiments, Sam68 activity is inhibited by administering Sam68 decoy peptides. Sam68 decoy peptides may be short polypeptides that competitively bind to complexes in which Sam68 functions, for example TNF signaling complex I and/or complex II. The binding of decoy peptides, rather than full-length Sam68, to these complexes can result in a non-functional complex, or inhibit complex assembly and integrity, thereby inhibiting Sam68.

In some embodiments, Sam68 is inhibited using nucleic acids that are capable of blocking the activity of, or inducing the degradation of a Sam68 mRNA. The polynucleotide sequence of the Sam68 mRNA is publicly available (Genbank accession #NM_006559). Such nucleic acids may exist in double-stranded, single-stranded, or partially double-stranded form. Such nucleic acids may be prepared by any conventional means typically used to prepare nucleic acids. Such nucleic acids can be from a human or a non-human mammal, derived from any recombinant source, synthesized in vitro or by chemical synthesis. For example, nucleic acids may be chemically synthesized using commercially available reagents and synthesizers by methods that are well-known in the art for example, the phosphotriester method of Matteucci, et al., (J. Am. Chem. Soc. 103:3185-3191, 1981) and/or using automated synthesis methods. (See, e.g., Gait, 1985, Oligonucleotide Synthesis: A Practical Approach, IRL Press, Oxford, England). In addition, larger DNA or RNA segments can readily be prepared by well-known methods, such as synthesis of a group of oligonucleotides that define various modular segments, followed by ligation of oligonucleotides to build the complete segment. The scope of the methods disclosed is not limited to naturally occurring Sam68 sequences; mutants and variants of Sam68 sequences are also covered by the scope of the methods disclosed.

In some embodiments Sam68 inhibitors are antisense nucleic acids. Such nucleic acids may include nucleic acids complementary to at least a portion of the Sam68 mRNA. In some embodiments, the complementary nucleic acid comprises a total of about 5 to about 100 or more nucleotides, more preferably about 10 to about 60 nucleotides, or about 10 to about 20 nucleotides. In some embodiments the Sam68 antisense has a sequence that is complementary to about 5 to about 100 nt or more of the Sam8 mRNA, preferably at least 5 nt of the Sam68 mRNA, more preferably at least 10 nt of the Sam68 mRNA, more preferably at least 15 nt of the Sam68 mRNA, and more preferably at least 20 nt of the Sam68 mRNA. In some embodiments, the complementary nucleic acid comprises a total of at least about 5, to about 26 nucleotides. In some embodiments, the sequence of the complementary nucleic acid comprises at least 5 nucleotides that are substantially complementary to the 5' region of a Sam68 mRNA or at least 5 nucleotides that are substantially complementary to the 3' region of a Sam68 mRNA. In some embodiments, the complementary nucleic acids are those that hybridize under stringent conditions to a mRNA encoding Sam68, for example the mRNA referred to by Genbank accession #NM_006559. In some embodiments an antisense nucleic acid is complementary to at least a portion of a Sam68 cDNA. The Sam68 antisense nucleic acid may comprise about 5 to 100 or more nucleic acids, for example, about 10 to about 60, 10 to about 30, or 10 to about 20 nucleotides. In some embodiments the Sam68 antisense comprises 5-20 or more nucleotides that are substantially complementary to a Sam68 cDNA, or at least 7-15 nucleotide that are substantially complementary to a Sam68 cDNA. In some embodiments complementary nucleic acids are those that hybridize under stringent conditions to a cDNA encoding Sam68, for example the cDNA referred to by Genbank accession #BC000717.

Antisense nucleic acids can be synthesized using methods known in the art, such as the methods described above, or may be purchased commercially. To increase stability and/or optimize delivery of the sense or antisense oligonucleotides, modified nucleotides or backbone modifications can be utilized. For example, modified nucleotides may include: linked nuclear acid (LNA), 2'-O-Me nucleotides, 2'-O-methoxyethyl, and 2' fluoro. Backbone modifications include, for example, phosphorothioate and phosphate. In some embodiments, antisense nucleic acids may be modified with cholesterol to enhance delivery to target cells. In some embodiments, synthetic sense or antisense nucleic acids are contacted with the target cell. In some embodiments antisense nucleic acids are provided systemically and taken up by cells. In other embodiments antisense nucleic acids are provided to specific cells, organs, or tissues. In some embodiments the antisense nucleic acid is provided directly. In other embodiments a vector may be provided such that the antisense nucleic acid is expressed in the desired cells. A vector may be provided such that it only expresses an antisense nucleic acid in a desired cell or organ type. For example a vector may contain transcriptional regulatory sequences that only produce a transcript in certain cell types. A vector may also be chemically modified so that it is only taken-up by a certain cell type, or within a certain organ. A vector may be configured so that it is transcriptionally silenced or degraded in certain cell types or organ types. Some exemplary vectors and methods of using such vectors are described below.

In some embodiments, the target cell is transfected with a plasmid encoding the sense or antisense nucleic acids. In some embodiments, the target cell is transduced with a virus or viral particle encoding the sense or antisense nucleic acids.

In some embodiments a Sam68 inhibitor is an siRNA directed against Sam68. siRNAs trigger the destruction of a target RNA, for example Sam68 mRNA, by the RNA interference (RNAi) pathway. siRNAs are typically short double-stranded RNAs comprising 2-nt overhangs on each 3' end. Within the cell, the dicer enzyme processes longer RNAs, for example double-stranded RNAs (dsRNAs) or short hairpin RNAs (shRNAs) to form siRNAs. dsRNA can be administered to a cell. Alternatively, an antisense RNA administered to a cell, or expressed within a cell can hybridize with an endogenous mRNA, thereby forming a dsRNA. An siRNA is integrated into the RNAi induced silencing complex (RISC), and targets RISC to mRNAs comprising sequences complementary to the siRNA. RISC mediates the cleavage of target mRNAs through an endonuclease activity, thereby reducing expression of the gene products encoded by the target mRNAs, for example Sam68. siRNAs are typically short RNA molecules of 19-25 nt, though even shorter siRNAs of 15-18 nt have been identified and may be used in some embodiments.

In some embodiments siRNAs are provided systemically and taken up by cells. In other embodiments siRNAs are provided to specific cells, organs, or tissues. In some embodiments, siRNAs are synthesized chemically or in a cell-based system and administered directly to a cell. In other embodiments, shRNAs or dsRNAs are provided directly to a cell. In other embodiments, a vector encoding an siRNA, antisense RNA, or sense and antisense RNA can be administered to a cell, thereby producing siRNAs within the cell by directly producing siRNAs, or by producing longer dsRNAs or shRNAs that are process by dicer. A vector may be provided such that it only expresses an siRNA in a desired cell or organ type. For example a vector may contain transcriptional regulatory sequences that only produce a transcript in certain cell types. For example, a vector may be chemically modified so that it is only taken-up by a certain cell type, or within a certain organ. For example, a vector may be configured so that it is transcriptionally silenced or degraded in certain cell types or organ types. Vectors and methods of using vectors are described below.

In some embodiments, siRNA mediated suppression of Sam68 is performed in mammalian cells by transfecting these cells with a plasmid encoding one or more siRNAs directed against Sam68. In some embodiments, siRNA-mediated suppression of Sam68 is performed by transducing mammalian cells with virus or virus particle encoding siRNA directed against Sam68. In some embodiments, non-targeting siRNAs are used as a control. In some embodiments, a Sam68 siRNA comprises a total of about 10 to about 50 nucleotides. for example, about 10 to about 50, about 15 to about 31, or about 15 to about 26 nucleotides. In some embodiments the Sam68 siRNA comprises at least 5-30 or more nucleotides that are substantially complementary to a Sam68 mRNA, for example at least 5-15 nt, 7-15 nt, 10-30 nt, 10-25, 10-20 nt, 15-30 nt, 15-25 nt, 15-20 nt, 20-30 nt, or 20-25 nt. An example of a Sam68 mRNA is that referred to by Genbank accession #NM_006559. An example of inhibiting Sam68 via siRNA is described in Example 2, below. Examples of siRNA sequences against human Sam68 include SEQ ID NO: 34, SEQ ID NO: 35, SEQ ID NO: 37, SEQ ID NO: 38, SEQ ID NO: 40, and SEQ ID NO: 41. Examples of siRNA sequences against mouse Sam68 include SEQ ID NO: 42, SEQ ID NO: 43, SEQ ID NO: 44, SEQ ID NO: 45.

In some embodiments a Sam68 inhibitor is an shRNA directed against Sam68. In some embodiments an shRNA comprises a stem region and a loop region. In some embodiments, the stem region is about 10 to about 40 nt, and the loop region is about 3 to about 40 nt. For example, the stem region may be about 10 to about 40 nt, about 10 to about 35 nt, about 15 to about 35 nt, about 15 to about 30 nt, about 20 to about 35 nt, about 20 to about 30 nt, about 25 to about 35 nt, or about 25 to about 30 nt. For example, the loop region may be about 3 to about 35 nt, about 3 to about 30 nt, about 3 to about 25 nt, or about 4 to about 23 nt. In some embodiments the Sam68 shRNA comprises at least 5-30 or more nucleotides that are substantially complementary to a Sam68 mRNA, for example at least 5-15 nt, 7-15 nt, 10-30 nt, 10-25, 10-20 nt, 15-30 nt, 15-25 nt, 15-20 nt, 20-30 nt, or 20-25 nt. An example of a Sam68 mRNA is that referred to by Genbank accession #NM_006559. In some embodiments shRNA is provided systemically and taken up by cells. In other embodiments it is provided to specific cells, organs, or tissues. In some embodiments the shRNA is provided directly to the cells. In other embodiments a vector may be provided such that the shRNA is expressed in the desired cells. A vector may be provided such that it only expresses an shRNA in a desired cell or organ type. For example a vector may contain transcriptional regulatory sequences that only produce a transcript in certain cell types. For example, a vector may be chemically modified so that it is only taken-up by a certain cell type, or within a certain organ. For example, a vector may be configured so that it is transcriptionally silenced or degraded in certain cell types or organ types. Vectors and methods of using vectors are described below. In some embodiments, mammalian cells are transduced with lentivirus or lentiviral particles expressing shRNA. In some embodiments, mammalian cells are transfected with plasmid encoding shRNA directed against Sam68. An example of inhibiting Sam68 via shRNA is described in Example 4, below. In some embodiments, non-targeting shRNAs are used as a control. Examples of shRNA sequences against human Sam68 are include SEQ ID NO: 33 (respective siRNAs are SEQ ID NOs: 34-35), SEQ ID NO: 36 (respective siRNAs are SEQ ID NOs: 37-38), and SEQ ID NO: 39 (respective siRNAs are SEQ ID NOs: 40-41).

It is not intended that the methods disclosed herein be limited by the source of the nucleic acids that are capable of inhibiting Sam68.

Human synthetic siRNA's are commercially available from Dharmacon. Human and mouse synthetic shRNA's are commercially available from Santa Cruz Biotechnology. It has been shown that siRNA-mediated inhibition of Sam68 can be performed in mammalian cells (Song et al, J. Pathology, 2010. 222: 227-37).

In some embodiments, Sam68 is inhibited by an antibody. Antibodies can be prepared using known methods. In addition, antibodies against human Sam68 and mouse Sam68 are commercially available, for example from Santa Cruz Biotechnology. As discussed in Example 5, below, the KH domain of Sam68 appears to play a role in Sam68 binding to the TNF receptor. In some embodiments, the epitope for the antibody comprises at least a portion of the KH domain of Sam68. In some embodiments, the epitope for the antibody comprises at least a portion of a proline rich region of Sam68, such as the polyproline tract of Sam68. In some embodiments, the epitope for the antibody comprises at least a portion of the RNA-binding (GSG) domain of Sam68. Antibodies may be delivered to cells directly in some embodiments. In other embodiments, a nucleic acid encoding the antibody is provided to cells, such that the antibody is expressed in the cell.

In some embodiments, a Sam68 inhibitor is a decoy peptide that lacks wild-type Sam68 activity, but competes with endogenous wild-typeSam68, thereby inhibiting Sam68 activity, such as the activity of complexes that require Sam68. For example, a Sam68 decoy peptide may compete with native Sam68 for binding to complex I and/or II. The binding of the decoy peptide may prevent the normal activity of the complex. For example, a Sam68 decoy peptide may bind to TNF signaling complex II, and prevent the binding of wild-type Sam68 to this complex, thereby resulting in a non-functional complex, preventing the formation of the complex, or inducing the dissociation of the complex. Thus, Sam68 is inhibited via expression of a Sam68 peptide. The full 443aa Sam68 protein sequence is available via Genbank Accession #Q07666. In some embodiments, a Sam68 polypeptide interferes with Sam68 activity, for example by binding to a complex in which Sam68 normally function, but lacking Sam68 activity. In some embodiments, the polypeptide comprises a total of about 5 to about 250 amino acid residues, and has a sequence comprising at least 5 amino acid residues of the Sam68 protein, more preferably at least 10 amino acid residues of the Sam68 protein, more preferably at least 15 amino acid residues of the Sam68 protein, and more preferably at least 20 amino acid residues of the Sam68 protein. In some embodiments, the polypeptide comprises sequence from the Sam68ΔKH (amino acids 157-256 deleted), the making and use of which is described in Example 5 below. In some embodiments, the polypeptide comprises a total of about 5 to about 343 amino acid residues of Sam68ΔKH, and has a sequence comprising at least 15 amino acid residues of Sam68ΔKH, more preferably at least 20 amino acid residues of Sam68ΔKH, more preferably at least 25 amino acid residues of Sam68ΔKH, and more preferably at least 30 amino acid residues of Sam68ΔKH.

As mentioned above, in some embodiments, once Sam68 is inhibited, levels of Sam68 expression or Sam68 activity are measured to assess the degree of Sam68 inhibition. For example, in a single cell, a population of cells, or a biological sample, levels of Sam68 protein may be measured, levels of Sam68 transcript may be measured, or the sequence or presence of endogenous Sam68 gene may be identified. Levels of Sam68 protein may be measured, for example, by immunoblotting, ELISA, immunoprecipitation, flow cytometry, or immunohistochemistry. Levels of Sam68 transcript may be identified, for example, by northern blotting or rt-PCR. The presence of endogenous Sam68 gene may be identified, for example, by PCR, Southern blotting, or sequencing the Sam68 locus. The sequence of endogenous Sam68 may be inferred by sequencing each Sam68 locus. A reduction in Sam68 activity in a given cell may be inferred from a reduction in Sam68 activity in a clone of that cell, in secretions from that cell, or in a population of cells from which that cell is derived. A reduction in Sam68 activity may also be inferred by monitoring markers of NF-κB activation, for example recruitment of complex I components to the plasma membrane, phosphorylation of IKK1, IKK2, and NEMO, ubiquitylation of RIP, ubiquitylation of the IκB proteins, IκBα degradation, translocation of NF-κB family transcription factors into the nucleus, and expression of an NF-κB target gene. Alternatively, a reduction in Sam68 may be inferred by monitoring markers of apoptosis, for example cleaved caspase 3, cleaved caspase 8, cleaved PARP, trypan blue exclusion of dead cells, neutral red assay, TUNEL staining, association of TRAF2 with TNFR, association of RIP with FADD, or levels of A20.

Expression Vectors:

In some embodiments, expression vectors that encode a Sam68 inhibitor are also useful for delivery of Sam 68 inhibitor to target cells. Examples of Sma68 inhibitors include siRNA, shRNA, antisense RNA, decoy RNA, decoy peptides, and antibodies.

In some embodiments, expression vectors that encode a wild-type Sam68 sequence, for example a Sam68 mRNA (e.g. the mRNA referred to by Genbank accession #NM_006559) or a Sam68 cDNA (e.g. the cDNA referred to by Genbank accession #BC000717) are useful for expression of functional Sam68 in at least one cell in which Sam68 function was lost. Thus the present invention also contemplates expression vectors that contain a Sam68 coding sequence and/or complement of a-Sam68 coding sequence, optionally associated with a regulatory element that directs the expression of the coding sequence in a target cell.

Sam68 and Sam68 inhibitor sequences are described in detail in the previous section. The choice of vector and/or expression control sequences to which the Sam68 or Sam68 inhibitor sequence is operably linked depends, as is well known in the art, on a number of factors, such as the functional properties desired, e.g., siRNA transcription, and the host cell to be transformed.

A vector contemplated by the present invention is preferably capable of directing replication in an appropriate host and of expression of a Sam68 or anti-Sam68 nucleic acid in a target cell. Vectors that can be used are well known in the art and include, but are not limited to, pUC8, pUC9, pBR322 and pBR329 available from BioRad Laboratories, (Richmond, Calif.), pPL and pKK223 available from Pharmacia (Piscataway, N.J.) for use in prokaryotic cells, and pSVL and pKSV-10 (Pharmacia), pBPV-1/pML2d (International Biotechnologies, Inc.), pCDNA and pTDT1 (ATCC, #31255), and pIRES.Puro vector (Invitrogen) for use in eukaryotic cells, as well as eukaryotic viral vectors such as adenoviral or retroviral vectors.

Vectors may include a selection gene whose expression confers a detectable marker such as a drug resistance. Typical selection genes encode proteins that confer resistance to antibiotics or other toxins, e.g., ampicillin, neomycin, methotrexate, or tetracycline, complement auxotrophic deficiencies, or supply critical nutrients withheld from the media. Such selection systems are well known in the art. The selectable marker can optionally be present on a separate plasmid and introduced by co-transfection.

Expression control elements that are used for regulating the expression of an operably linked coding sequence are known in the art and include, but are not limited to, inducible promoters, constitutive promoters, enhancers, and other regulatory elements. In some embodiments an inducible promoter is used that is readily controlled, such as being responsive to a nutrient in the target cell's medium. In some embodiments, the promoter is the U6 promoter or CMV promoter. A vector may be provided such that it only expresses an siRNA, shRNA, antisense RNA, sense and antisense RNA, decoy RNA, or decoy peptide in a desired cell or organ type. For example a vector may contain transcriptional regulatory sequences that only produce a transcript in certain cell types. For example a vector may contain transcriptional regulatory sequences that repress expression of a transcript in certain cell types. For example, a vector may be chemically modified so that it is only taken-up by a certain cell type, or within a certain organ. For example, a vector may be configured so that it is transcriptionally silenced or degraded in certain cell types or organ types. Vectors and methods of using vectors are described below Other methods, vectors, and target cells suitable for adaptation to the expression of Sam68 or Sam68 inhibitor nucleic acids in target cells are well known in the art and are readily adapted to the specific circumstances.

Delivery of Oligonucleotides

In some embodiments, methods of delivering oligonucleotides are provided. In some embodiments, oligonucleotides are used to inhibit Sam68 in a mammalian cell. In some embodiments, oligonucleotides are used to express a therapeutically effective amount of an oligonucleotide configured to inhibit Sam68 activity such as siRNA, antisense and shRNA. In some embodiments, oligonucleotides are used to express functioning Sam68 in a mammalian cell, for example in a cell in which endogenous Sam68 activity has been reduced or eliminated, such as by a mutation. In some embodiments, oligonucleotides are used to express a therapeutically effective amount of an inhibitor of Sam68.

Reagents for delivery of Sam68 and Sam68 inhibitor nucleic acids and expression vectors can include, but are not limited to protein and polymer complexes (polyplexes), lipids and liposomes (lipoplexes), combinations of polymers and lipids (lipopolyplexes), and multilayered and recharged particles. Transfection agents may also condense nucleic acids. Transfection agents may also be used to associate functional groups with a polynucleotide. Functional groups can include cell targeting moieties, cell receptor ligands, nuclear localization signals, compounds that enhance release of contents from endosomes or other intracellular vesicles (such as membrane active compounds), and other compounds that alter the behavior or interactions of the compound or complex to which they are attached (interaction modifiers). For delivery in vivo, complexes made with sub-neutralizing amounts of cationic transfection agent may be preferred. In some embodiments, at least one mammalian cell is transduced with lentivirus or lentiviral particles expressing an anti-Sam68 inhibitor such as an anti-Sam68 shRNA. In some embodiments, at least one mammalian cell is transfected with plasmid encoding a Sam68 inhibitor, such as an anti-Sam68 shRNA. In some embodiments, transfection is performed using Lonza nucleofector device. In some embodiments, transfection is performed using Lipofectamine 2000 reagent according to the manufacturer's (Invitrogen) instructions. In some embodiments, transfection is performed by calcium phosphate precipitation method (Sambrook et al, 1989. Molecular cloning: A Laboratory Manual, Second Edition. Cold Spring Harbor, N.Y.: Cold Spring Harbor Laboratory Press). Other applicable methods are known in the art.

In some embodiments, polycations are mixed with polynucleotides for delivery to a cell. Polycations are a very convenient linker for attaching specific receptors to DNA and as result, DNA/polycation complexes can be targeted to specific cell types. Here, targeting is preferably to cells involved in innate immunity. An endocytic step in the intracellular uptake of DNA/polycation complexes is suggested by results in which functional DNA delivery is increased by incorporating endosome disruptive capability into the polycation transfection vehicle. Polycations also cause DNA condensation. The volume which one DNA molecule occupies in complex with polycations is drastically lower than the volume of a free DNA molecule. The size of DNA/polymer complex may be important for gene delivery in vivo. In some embodiments, nucleic acids targeted against Sam68 and a transfection reagent are delivered systematically such as by injection. In other embodiments, they may be injected into particular areas comprising target cells, such as particular organs, for example the bone marrow.

Polymer reagents for delivery of nucleic acids and expression vectors may incorporate compounds that increase their utility. These groups can be incorporated into monomers prior to polymer formation or attached to polymers after their formation. A siRNA, shRNA, or expression vector transfer enhancing moiety is typically a molecule that modifies a nucleic acid complex and can direct it to a cell location (such as tissue cells) or location in a cell (such as the nucleus) either in culture or in a whole organism. By modifying the cellular or tissue location of the complex, the desired localization and activity of the nucleic acid, such as siRNA, shRNA, or expression vector can be enhanced. The transfer enhancing moiety can be, for example, a protein, peptide, lipid, steroid, sugar, carbohydrate, nucleic acid, cell receptor ligand, or synthetic compound. The transfer enhancing moieties can enhance cellular binding to receptors, cytoplasmic transport to the nucleus and nuclear entry or release from endosomes or other intracellular vesicles.

Nuclear localizing signals can also be used to enhance the targeting of the nucleic acid, such as siRNA, shRNA, or expression vector into proximity of the nucleus and/or its entry into the nucleus. Such nuclear transport signals can be a protein or a peptide such as the SV40 large Tag NLS or the nucleoplasmin NLS. These nuclear localizing signals interact with a variety of nuclear transport factors such as the NLS receptor (karyopherin alpha) which then interacts with karyopherin beta. The nuclear transport proteins themselves could also function as NLS's since they are targeted to the nuclear pore and nucleus.

Compounds that enhance release from intracellular compartments can cause nucleic acid release from intracellular compartments such as endosomes (early and late), lysosomes, phagosomes, vesicle, endoplasmic reticulum, Golgi apparatus, trans Golgi network (TGN), and sarcoplasmic reticulum and could be used to aid delivery of Sam68 inhibitors. Release includes movement out of an intracellular compartment into cytoplasm or into an organelle such as the nucleus. Such compounds include chemicals such as chloroquine, bafilomycin or Brefeldin Al and the ER-retaining signal (KDEL sequence), viral components such as influenza virus hemagglutinin subunit HA-2 peptides and other types of amphipathic peptides.

Cellular receptor moieties are any signal that enhances the association of a nucleic acid, such as siRNA, shRNA, or expression vector with a cell. Enhanced cellular association can be accomplished by either increasing the binding of the polynucleotide or polynucleotide complex to the cell surface and/or its association with an intracellular compartment, for example: ligands that enhance endocytosis by enhancing binding the cell surface. Cellular receptor moieties include agents that target to asialoglycoprotein receptors by using asialoglycoproteins or galactose residues. Other proteins such as insulin, EGF, or transferrin can be used for targeting. Peptides that include the RGD sequence can also be used to target many cells. Chemical groups that react with sulfhydryl or disulfide groups on cells can also be used to target many types of cells. Folate and other vitamins can also be used for targeting. Other targeting groups include molecules that interact with membranes such as lipids fatty acids, cholesterol, dansyl compounds, and amphotericin derivatives. In addition viral proteins could be used to target cells.

In some embodiments, oligonucleotides can be delivered systematically. In some embodiments, oligonucleotides can be delivered to a particular cell, cell population, organ, tissue, or region. In some embodiments, oligonucleotides can be delivered in vivo. In some embodiments, oligonucleotides can be delivered ex vivo. Oligonucleotides can be delivered, for example, by injection or other methods are known in the art.

Inhibition of TNF-Dependent Signaling

Methods are provided for regulating cytokine receptor activity, the methods comprising administering one or more Sam 68 inhibitors to a cell or cells in which cytokine receptor activity is to be regulated. In some embodiments, TNF-dependent signaling can be reduced, while TNF-independent signaling is reduced to a lesser degree or not at all. In some embodiments, the TNF-dependent signaling is NF-κB signaling. In some embodiments, the TNF-dependent signaling is apoptosis via the extrinsic pathway.

In some embodiments, a patient is diagnosed as suffering from a disease or disorder associated with TNF-dependent signaling. In some embodiments, TNF-dependent signaling is inhibited by inhibiting Sam68, using the methods described herein. In some embodiments, prior to inhibition of Sam68, markers of TNF-dependent signaling are monitored. In some embodiments, following inhibition of Sam68, markers of TNF-dependent signaling are monitored to verify that TNF-dependent signaling has been inhibited.

Inhibition of NF-κB Signaling:

Methods are provided for inhibiting TNF-dependent NF-κB signaling in a mammalian cell or cells by inhibiting Sam68. In some embodiments, the inhibition is performed in vivo. In some embodiments, the inhibition is performed in vitro. In some embodiments, the inhibition is performed ex vivo. In some embodiments, the cell is from a cell line, is grown in cell culture, or is derived from a biological sample. In some embodiments, at least one cell is provided, and Sam68 is inhibited in the cell or cells.

In some embodiments, a Sam68 inhibitor is administered to a cell or cells in which NF-κB signaling is to be inhibited. In some embodiments the Sam68 inhibitor is an antisense RNA, siRNA, dsRNA, shRNA, decoy peptides, or decoy RNA, provided systemically and taken up by cells, or a Sam68 antibody provided systematically to cells. In other embodiments antisense RNA, siRNA, dsRNA, shRNA, decoy peptides, decoy RNA, or antibodies is provided to specific cells, organs, or tissues. In some embodiments, Sam68 inhibitor RNAs such as siRNA, shRNA, dsRNA, or antisense RNAs are synthesized chemically or in a cell-based system and administered to a cell. In some embodiments, a vector encoding a Sam68 siRNA, Sam68 shRNA, Sam68 antisense RNA, dsRNA, Sam68 decoy peptide, or Sam68 decoy RNA is administered to a cell, thereby producing siRNAs within the cell through the mechanisms described above. A vector may be provided such that it only expresses an siRNA, shRNA, antisense RNA, sense and antisense RNA, decoy RNA, or decoy peptide in a desired cell or organ type.

A vector may contain transcriptional regulatory sequences that only produce a transcript in certain cell types. A vector may be chemically modified so that it is only taken-up by a certain cell type, or within a certain organ. A vector may be configured so that it is transcriptionally silenced or degraded in certain cell types or organ types. Vectors and methods of using vectors are described herein.

In some embodiments, monitoring NF-κB is useful for identifying a cell or cells in need of Sam68 inhibition. Numerous cancer cells, or cells with a pre-cancer phenotype have been found to exhibit activation of NF-κB signaling, including, but not limited to B cell tumors (e.g. Hodgkin's and non-Hodgkin's lymphomas) and multiple myeloma tumors. A cancerous or-precancerous phenotype or other disease state may be identified or characterized by monitoring markers of NF-κB activation. For example, elevated NF-κB activation may be used to select a patient for treatment with anti-Sam68. Thus, in some embodiments, it will be beneficial to a patient to inhibit NF-κB signaling associated with a disease state. In some embodiments, administration of a therapeutically effective amount of Sam68 inhibitor can be used to inhibit NF-kB signaling.

In some embodiments, inhibition of TNF-dependent NF-kB signaling is verified following inhibition of Sam68. Signaling may also be measured prior to Sam68 inhibition, for example to determine a baseline level of activity. In some embodiments, markers of NF-κB activation are monitored in the cell, one or more clones of the cell, one or more cells from the same population as the cell, or a biological sample derived from the same organism as the cell. In some embodiments, the cell is contacted with a TNF receptor agonist—for example TNFα—in order to stimulate TNF-dependent NF-kB signaling, should any NF-kB signaling activity remain. Monitoring of markers may be used to determine whether the Sam68-inhibited cell or a Sam68+ control cell exhibited NF-κB activation, and whether inhibition of Sam68 resulted in a reduction in NF-κB activation. One skilled in the art will appreciate that inhibition of Sam68 will reduce NF-κB signaling activity if the NF-κB pathway exhibits TNF-dependent NF-κB activation. If, for example, a constitutive mutation in the TNF receptor is causing an increase in NF-kB activation, inhibition of Sam68 will reduce NF-kB signaling activity. However, inhibition of Sam68 will not reduce NF-κB signaling activity if the pathway exhibits substantially TNF-independent NF-κB activation. If for example, the NF-kB pathway is activated solely via a mutation that increases IL-1 activity, inhibition of Sam68 will not reduce NF-kB signaling activity. Examples of NF-kB inducers can be found at (http://www.bu.edu/nf-kb/physiological-mediators/inducers/).

In some embodiments, following inhibition of Sam68, inhibition of NF-kB signaling is verified by monitoring markers of NF-kB signaling. Markers of NF-κB activation are referred to in the broadest sense, and include molecules that exhibit a different conformation, covalent modification (for example, ubiquitylation, phosphorylation, methylation, acetylation, SUMOylation), proteolysis reaction, subcellular localization, copy number, alternative splicing event, transcriptional event, membership in a complex of proteins and/or nucleic acids, or dissociation from a complex of proteins and/or nucleic acids, in a cell that has undergone NF-κB activation in comparison to a cell that has not undergone NF-κB activation. Examples of markers of NF-κB activation include recruitment of complex I components to the plasma membrane, phosphorylation of IKK1, IKK2, and NEMO, ubiquitylation of RIP, ubiquitylation of the IκB proteins, IκBα degradation, translocation of NF-κB family transcription factors into the nucleus, and expression of an NF-κB target gene. Examples of NF-κB target genes can be found in (Pahl, HL. "Activators and target genes of Rel/NF-kappaB transcription factors." Oncogene. 1999 18: 6853-66; and http://www.bu.edu/nf-kb/gene-resources/target-genes/). By way of example only, markers of NF-κB activation can be monitored in the cell, a clone of the cell, a population of cells, or a biological sample using, for example, flow cytometry, immunoblotting, immunoprecipitation, enzyme-linked immunosorbent assay (ELISA), immunohistochemistry, in situ hybridization, quantitative RT-PCR, microarray analysis, RNA-seq, Mass spectrometry based proteomics, gel shift assays, chromatin immunoprecipitation, or transcription factor binding assays.

In some embodiments, a candidate Sam68 inhibitor may be validated for its ability to reduce Sam 68 expression, reduce Sam68 activity, or prevent, delay, ameliorate, stabilize, or treat a disease or disorder characterized by TNF-dependent signaling. Candidate Sam68 inhibitors that are found to modulate TNF-dependent signaling may be used to stop or reduce disease indications in a patient suffering from a disease associated with TNF-dependent signaling. Examples of candidate Sam68 inhibitors include antisense RNA, siRNA, shRNA, dsRNA, decoy RNA, decoy peptides, and antibodies.

A candidate Sam68 inhibitor can be validated for its ability to inhibit Sam68 by monitoring markers of Sam68 activity. Examples of markers of Sam68 activity include Sam68 transcript levels, Sam68 protein levels, ubiquitylated RIP, cleaved caspase 3, cleaved caspase 8, cleaved PARP, trypan blue exclusion of dead cells, neutral red assay, TUNEL staining, association of TRAF2 with TNFR, association of RIP with FADD, levels of A20 protein, as well as markers of activation of NF_kB signaling, which are discussed above.

A candidate Sam68 inhibitor that has been found to inhibit Sam68 (and TNF-dependent signaling), can be administered to an animal in an animal model of disease associated with TNF-dependent signaling and tested for its ability to reduce disease indications. For example, a Sam68 inhibitor compound can be tested in an animal model of NF-kB dependent lymphoma for its ability to reduce counts of abnormal lymphocytes. In some embodiments, a candidate compound can be directly administered to the blood or bone marrow an animal in an animal model of disease associated with TNF-dependent signaling and the ability of the candidate compound to treat or reduce disease symptoms can be tested, for example by monitoring makers of TNF-dependent signaling.

In some embodiments, candidate compounds that reduce TNF-dependent signaling are selected. In other embodiments, compounds that do not reduce TNF-dependent signaling are eliminated from consideration as therapeutic agents for the treatment of a disease associated with TNF-dependent signaling.

Compounds identified as a compound capable of preventing and/or reducing TNF-dependent signaling may be used, for example, as therapeutics to treat or prevent the onset of a disease or disorder characterized by TNF-dependent signaling.

Treatment of a Disease Associated with NF-kB Signaling

In some embodiments, methods are provided for treating a patient suffering from a disease or disorder associated with NF-kB signaling. Examples of diseases or disorders associated with NF-kB signaling include various leukemias and lymphomas, for example Hodgkin's lymphoma, non-Hodgkin's lymphoma, chronic lymphocyte leukemia, and multiple myeloma; solid tumors, for example colorectal cancer, prostate cancer, gastric cancer, ovarian cancer, breast cancer, pancreatic cancer, thyroid cancer, bladder cancer, melanomas, and on-small cell lung carcinoma; inflammation-associated cancers; and other immune or inflammatory disorders, for example rheumatoid arthritis, artherosclerosis, multiple sclerosis, chronic inflammatory demyelinating polyradiculoneuritis, asthma, inflammatory bowel disease, helicobacter pylori-associated gastritits, Type I diabetes, Type II diabetes, and systemic inflammatory response syndrome. In some embodiments, the disease or disorder is associated with a gain-of-function mutation in a positive regulator, or a loss-of-function mutation in a negative regulator in the NF-kB pathway. In some embodiments, a patient suffers from a disease associated with NF-kB activation, and the patient would benefit from reduction in NF-kB activity. For example NF-kB may be at least a partial cause of the disease, NF-kB may exacerbate at least one indication of the disease, or NF-kB signaling may interfere with the mechanism of action for a therapeutic administered to treat the disease. In some embodiments, the health concerns of the patient, or the etiology of the disease or disorder is such that it is desirable to inhibit TNF-dependent NF-kB signaling. In some embodiments, only TNF-dependent NF-kB signaling is inhibited, while TNF-independent NF-kB signaling, for example through the IL-pathway, is not inhibited or is inhibited to a lesser degree.

In some embodiments, a diagnosis is performed on a patient to identify whether the patient is in need of treatment to reduce TNF-dependent NF-kB signaling. In some embodiments, markers are observed to determine whether the disease or disorder is associated with TNF-signaling. One skilled in the art will appreciate that a patient with a disease or disorder associated with TNF-dependent NF-kB signaling will exhibit markers of TNF-dependent NF-kB signaling. Example of markers include association of TRAF2 with TNFR, and ubiquitylation of RIP. One skilled in the art will also appreciate that markers of NF-kB activation may be indicative of a disease or disorder associated with TNF-dependent NF-kB activation. Examples of markers of NF-κB activation include recruitment of complex I components to the plasma membrane, phosphorylation of IKK1, IKK2, and NEMO, ubiquitylation of the IκB proteins, IκBα degradation, translocation of NF-κB family transcription factors into the nucleus, and expression of an NF-κB target gene.

In some embodiments, the patient is diagnosed with the disease or disorder. In some embodiments, the diagnosis comprises monitoring at least one marker of NF-kB signaling, for example, at least one marker described above. In some embodiments, the presence of at least one marker of NF-kB signaling is indicative of the disease. In some embodiments, the absence of at least one marker of NF-kB signaling is indicative of the disease. In some embodiments, an increase in at least one marker of NF-kB signaling is indicative of the disease. In some embodiments, a decrease in at least one marker of NF-kB signaling is indicative of the disease. In some embodiments, the diagnosis comprises measuring at least one marker of Sam68 activity. In some embodiments, the presence of at least one marker of Sam68 activity is indicative of the disease. In some embodiments, the absence of at least one marker of Sam68 activity is indicative of the disease. In some embodiments, an increase in at least one marker of Sam68 activity is indicative of the disease. In some embodiments, a decrease in at least one marker of Sam68 activity is indicative of the disease. For example, levels of Sam68 protein may be measured, levels of Sam68 transcript may be measured, or the sequence or presence of endogenous Sam68 gene may be identified. Levels of Sam68 protein may be measured by immunoblotting, ELISA, immunoprecipitation, flow cytometry, or immunohistochemistry. Levels of Sam68 transcript may be identified by northern blotting or RT-PCR. The presence of endogenous Sam68 gene may be identified by PCR, Southern blotting, or sequencing the Sam68 locus. The sequence of endogenous Sam68 may be inferred by sequencing at least one Sam68 locus in a cell or in a population of cells.

In some embodiments, Sam68 is inhibited in at least one cell of the patient, using the methods described above. In some embodiments, a therapeutically effective amount of Sam68 inhibitor is provided. In some embodiments, a Sam68 inhibitor is provided to the cell or cells in which Sam68 is to be inhibited. In some embodiments the Sam68 inhibitor is an antisense RNA, siRNA, dsRNA, shRNA, decoy peptide, or decoy RNA provided systemically and taken up by cells, or a Sam68 antibody provided systematically to cells. In other embodiments antisense RNA, siRNA, dsRNA, shRNA, decoy peptides, decoy RNA, or antibodies is provided to specific cells, organs, or tissues. In some embodiments, Sam68 inhibitor RNAs such as siRNA, shRNA, dsRNA, or antisense RNAs is synthesized chemically or in a cell-based system and administered directly to a cell. In some embodiments, a vector encoding a Sam68 siRNA, Sam68 shRNA, Sam68 antisense RNA, dsRNA, Sam68 decoy peptide, or Sam68 decoy RNA is administered to a cell, thereby producing siRNAs within the cell through the mechanisms described above. A vector may be provided such that it only expresses an siRNA, shRNA, antisense RNA, sense and antisense RNA, decoy RNA, or decoy peptide in a desired cell or organ type.

In some embodiments, following inhibition of Sam68, inhibition of Sam68 is verified by monitoring at least one marker of Sam68 activity, as described above. In some embodiments, following inhibition of Sam68, inhibition of NF-kB signaling is verified by monitoring the markers of NF-kB signaling described above.

Inhibition of Apoptosis:

In some embodiments, methods are provided for inhibiting TNF-dependent activation of the extrinsic apoptotic pathway in a mammalian cell. In some embodiments, the inhibition is performed in vivo. In some embodiments, the inhibition is performed in vitro. In some embodiments, the inhibition is performed ex vivo. In some embodiments, the cell is from a cell line, is grown in cell culture, or is derived from a biological sample. Sam68 is inhibited in the cell, as described above.

In some embodiments, markers of apoptotic activation are monitored in the cell, one or more clones of the cell, one or more cells from the same population as the cell, or a biological sample derived from the same organism as the cell. Monitoring of markers of apoptotic activation may be used to determine whether the Sam68-inhibited cell or a Sam68+ control cell exhibited activation of the apoptotic pathway, and whether inhibition of Sam68 resulted in a reduction in markers of apoptotic activation. One skilled in the art will appreciate that inhibition of Sam68 will reduce apoptosis if the apoptotic pathway exhibits TNF-dependent activation of the extrinsic apoptotic pathway, but will not reduce apoptotic pathway activation, or will reduce activation to a lesser extent, if the pathway exhibits TNF-independent activation of the extrinsic apoptotic pathway or activation of the intrinsic apoptotic pathway.

In some embodiments, following inhibition of Sam68, inhibition of apoptosis is verified by monitoring markers of apoptosis. In some embodiments, the cell is contacted with a TNF receptor agonist—for example TNFα—in order to stimulate TNF-dependent apoptosis, should any apoptotic activity remain. Inhibition the apoptosis can be verified by monitoring markers of apoptotic activation. In some embodiments, the presence of a marker indicates the inhibition of apoptosis. For example, the presence of neutral red can indicate the inhibition of apoptosis. In some embodiments, the absence of a marker indicates the inhibition of apoptosis. For example, the absence of trypan blue can indicate the inhibition of apoptosis. In some embodiments, an increase in a marker can indicate the inhibition of apoptosis. For example, an increase in procaspase 3 relative to cleaved caspase 3 can indicate inhibition of apoptosis. In some embodiments, a decrease in a marker can indicate the inhibition of apoptosis. For example, a decrease in cleaved PARP can indicate inhibition of apoptosis. Markers of apoptotic activation are referred to in the broadest sense, and include molecules, cellular process, cellular morphologies, or changes in cell populations that occur when the cell or cells in that population undergo apoptosis. By way of example only, examples of "markers of apoptotic activation" include cleaved PARP, cleaved Caspase 3, cleaved Caspase 8 trypan blue exclusion of dead cells, neutral red assay, and TUNEL staining. By way of example only, markers of apoptotic activation may be monitored using flow cytometry, immunoblotting, immunoprecipitation, ELISA, immunohistochemistry, in situ hybridization, quantitative RT-PCR, or microarray analysis. One skilled in the art will recognize that cleaved PARP, cleaved Caspase 3, cleaved Caspase 8, trypan blue exclusion of dead cells, lack of uptake of vital red dye in the neutral red assay, and positive signal in TUNEL staining indicate activation of the apoptosis pathway. One skilled in the art will recognize that uncleaved PARP, uncleaved Caspase 3 (aka procaspase 3), cleaved Caspase 8 (aka procaspase 8), trypan blue uptake, uptake of vital red dye in the neutral red assay, and negative signal in TUNEL staining indicate activation of the apoptosis pathway. By way of example only, markers of apoptotic activation may be monitored using flow cytometry, immunoblotting, immunoprecipitation, ELISA, immunohistochemistry, in situ hybridization, quantitative RT-PCR, or microarray analysis Treatment of a Disease or Disorder Associated with TNF-Dependent Activation of the Extrinsic Apoptosis Pathway In some embodiments, methods are provided for treating a patient suffering from a disease or disorder associated with TNF-dependent activation of the extrinsic apoptosis pathway. Examples of diseases or disorders caused by excess apoptosis include AIDS; neurodegenerative diseases, for example Alzheimer's disease, Amyotrophic lateral sclerosis, Parkinson's disease, retinitis pigmentosa, and epilepsy; hemotologic diseases, for example aplastic anemia, myelodysplastic syndrome, T CD4+ lymphocytopenia, G6PD deficiency; and tissue damage diseases, for example myocardial infarction, cerebrovascular accident, stroke, ischemic renal damage, and polycystic kidney. In some embodiments, the patient is in need of, or will benefit from inhibition of apoptosis through the extrinsic pathway. For example, the disease or disorder may be caused, at least in part, by a gain-of-function mutation in a positive regulator, or a loss-of-function mutation in a negative regulator of the TNF-dependent extrinsic apoptosis pathway. In some embodiments, the health concerns of the patient, or the etiology of the disease or disorder is such that it is desirable to inhibit only TNF-dependent extrinsic apoptosis signaling, while not interfering with TNF-independent apoptosis, for example through the fas-induced pathway.

In some embodiments, a diagnosis is performed on the patient to determine whether the patient is in need of treatment to inhibit apoptosis or will benefit from inhibition of apoptosis through the extrinsic pathway. In some embodiments, the diagnosis comprises monitoring at least one marker of apoptosis, for example, at least one marker described above. In some embodiments, the presence of a marker indicates the patient is in need of treatment to inhibit apoptosis, or will benefit from inhibition of apoptosis through the extrinsic pathway. In some embodiments, the absence of a marker indicates the patient is in need of treatment to inhibit apoptosis, or will benefit from inhibition of apoptosis through the extrinsic pathway. In some embodiments, the increase of a marker indicates the patient is in need of treatment to inhibit apoptosis, or will benefit from inhibition of apoptosis through the extrinsic pathway. In some embodiments, the decrease of a marker indicates the patient is in need of treatment to inhibit apoptosis, or will benefit from inhibition of apoptosis through the extrinsic pathway. For example, levels of Sam68 protein may be measured, levels of Sam68 transcript may be measured, or the sequence or presence of endogenous Sam68 gene may be identified. For example, levels of Sam68 protein may be measured by immunoblotting, ELISA, immunoprecipitation, flow cytometry, or immunohistochemistry. For example, levels of Sam68 transcript may be identified by northern blotting, microarray analysis, or RT-PCR. The presence of endogenous Sam68 gene may be identified by PCR, Southern blotting, or sequencing the Sam68 locus. The sequence of endogenous Sam68 may be inferred by sequencing at least one Sam68 locus in a cell or in a population of cells.

In some embodiments, markers are observed to determine whether the disease is associated with TNF-dependent signaling. One skilled in the art will appreciate that a patient with a disease associated with activation of TNF-dependent extrinsic apoptosis will exhibit markers of TNF-dependent apotosis. Examples of markers include association of RIP with FADD, and activation of caspase 8. One skilled in the art will also appreciate that markers of apoptotic activation may be indicative of a disease associated with TNF-dependent activation of the extrinsic apoptosis pathway. Examples of markers of apoptotic activation include cleaved caspase 3, cleaved PARP, neutral red exclusion, trypan blue exclusion, and TUNEL staining.

In some embodiments, Sam68 is inhibited in at least one cell of the patient, using the methods described above. In some embodiments, a therapeutically effective amount of Sam68 inhibitor is administered to the patient. In some embodiments, all substantial Sam68 expression or function is inhibited. In some embodiments, Sam68 expression or activity is reduced, but is not completely inhibited.

In some embodiments, following inhibition of Sam68, inhibition of Sam68 is verified by monitoring at least one marker of Sam68 activity, as described above.

In some embodiments, following inhibition of Sam68, inhibition of TNF-dependent extrinsic apoptosis is verified by monitoring the markers of apoptotic activation described above.

Disruption of TRAF Association with Complex I of TNFR Signaling

"Complex I" is a complex of proteins that is formed in response to TNF stimulation in mammalian cells. Complex I is typically formed within minutes after TNF stimulation, and is typically associated with the plasma membrane. In healthy cells, Complex I comprises the proteins TNF Receptor (TNFR), TRADD, RIP, TRAF2, cIAPs and IKKs. Several studies suggest that K63-linked ubiquitylation of RIP by the E3 ligases TRAF2 and cIAPs in the complex I as a crucial determinant in the activation of NF-κB by TNFR1 (Ea et al., 2006. Mol Cell 22, 245-257.) (Alvarez, 2010. Nature 465, 1084-1088) (Varfolomeev et al., 2008. The Journal of biological chemistry 283, 24295-24299.)

In some embodiments, methods are provided for the disruption of TRAF2 association with Complex I. As discussed in Example 5 below, inhibition of Sam68 interferes with association of TRAF2 with complex I, and interferes with Rip ubiquitylation in complex I. In some embodiments, a cell is identified, the cell having increased NF-kB signaling activity. In some embodiments, Sam68 is inhibited in the cell, using the methods described above. In some embodiments, markers of Complex I integrity and activity are measured to verify that TRAF2 binding Complex I has been disrupted. Examples of these markers include ubiquitylated RIP, and association of TRAF2 with TNFR. In some embodiments, ubiquitylation of RIP and association of TRAF2 with TNFR can be measured by immunoprecipitation of the receptor-associated complex, for example, by using a GST-TNFR to immunoprecipitate complex components, and then immunoblotting the components that were recruited. An example of measuring Complex I integrity and RIP ubiquitylation is described in Example 5, below.

Disruption of RIP Binding and Caspase8 Activation of Complex II of TNFR Signaling "Complex II" is a complex of proteins that is formed in response to TNF stimulation of mammalian cells. Complex II is typically formed hours after TNF stimulation, and is found in the cytoplasm. In healthy cells, Complex II comprises the proteins TRADD, RIP, TRAF2, caspase8, and FADD. Caspase8 activation in complex II instigates the apoptotic process (Micheau and Tschopp, 2003. Cell 114, 181-190.) (Wang et al., 2008. Cell 133, 693-703.).

In some embodiments, methods are provided for monitoring components of Complex II. In some embodiments, a cell is identified, the cell having increased apoptotic activity. In some embodiments, the increased apoptotic activity is via the TNF-dependent extrinsic apoptotic pathway. As discussed in Example 5 below, inhibition of Sam68 interferes with Comple II integrity, specifically interfering with RIP binding to complex II, and Caspase 8 activation. In some embodiments, Sam68 is inhibited in the cell, using the methods described above, thereby interfering with RIP binding to complex II, and thereby interfering with Caspase8 activation in complex II. In some embodiments, markers of Complex II activity are monitored to verify disruption of the activity of the complex. For example, Complex II can be immunoprecipitated through FADD, and immunoprecipitates can be analyzed for the presence of RIP using immunoblotting. As another example, caspase3 activation and PARP cleavage may be monitored in the cell to infer whether RIP was recruited to Complex II, or to infer whether Caspase8 was activated. An example of measuring Complex II integrity and activity is described in Example 5, below.

Increasing Extrinsic Apoptotic Pathway Activity:

In light of the surprising finding that Sam68 is necessary for activation of the extrinsic apoptotic pathway, some cells in a disease state may fail to undergo apoptosis, for example due to a reduction or loss of Sam68 activity. By way of example, diseases associated with defects in include cancers, for example colorectal cancer, glioma, hepatic cancer, neuroblastoma, leukemias and lymphomas, and prostate cancer; viral infections, for example adenovirus infections and baculovirus infections; autoimmune diseases, for example myasthenia gravis and stemic lupus erythematosis; inflammatory diseases, for example bronchial asthma, inflammatory intestinal disease, and pulmonary inflammation. Methods are provided for increasing activity of the extrinsic apoptotic pathway.

In some embodiments, the cell has suffered a decrease in extrinsic apoptosis pathway activity below a basal level. In some embodiments, the cell has suffered an elimination of substantially all extrinsic apoptosis activity. In some embodiments, there is some extrinsic apoptosis activity, but an increase is desirable.

In some embodiments, methods are provided for increasing activity of the extrinsic apoptotic pathway. As provided in Example 4 below, inhibition of Sam68 blocks activation of the pro-apoptotic pathway. For example, a tumor cell may be unable to undergo apoptosis due to a mutation inhibiting Sam68 activity. In some embodiments, a mammalian cell is identified as being unable to activate the pro-apoptotic pathway, or is otherwise in need of activation or increased activation of apoptosis. Markers of apoptotic activation may be monitored in the cell, in a population of cells that contains the cell, in a clone of the cell, or in a biological sample from the same organism that the cell was derived from. For example, a cell with defective activation of the extrinsic apoptotic pathway will not express markers of the activated extrinsic apoptosis pathway. For example, a cell with reduced levels of Sam68 transcript or protein, or a mutation in Sam68 will exhibit reduced activity in the extrinsic apoptosis pathway.

In some embodiments, a reduction in Sam68 activity is identified in the mammalian cell, using the methods described above to measure Sam68 activity or expression levels.

In some embodiments, Sam68 is provided to the cell to increase activity of the extrinsic apoptosis pathway. In some embodiments, a nucleic acid construct encoding wild-type Sam68 or tagged wild-type Sam68 is introduced to the cells for which increase of pro-apoptotic pathway activity is desired. Methods of introducing nucleic acid constructs into cells are well-known in the art, and are described above. For example, the wild-type Sam68 may be introduced via transfection, nucleofection, transduction, or methods known in the art. In some embodiments, the construct expressing Sam68 is introduced to a population of cells simultaneously. In some embodiments, the construct expressing Sam68 is introduced to a whole tissue or organ. In some embodiments, the construct expressing Sam68 is introduced to a living mammal.

In some embodiments, Sam68 expression is increased in the cell. In some embodiments, a transcription factor that increases Sam68 expression is provided to the cell. In some embodiments, a nucleic acid construct encoding the transcription factor that increases Sam68 expression is provided to the cell. In some embodiments, a transcription factor that represses Sam68 expression is inhibited. For example, a transcription factor that inhibits Sam68 expression may be targeted with siRNA, shRNA, antisense RNA, sense RNA, or a decoy peptide using methods described above. By way of example only, a transcription factor that inhibits Sam68 expression may also be targeted with a small molecule inhibitor.

In some embodiments, functional Sam68 protein is provided to the cell.

In some embodiments, an increase in the expression and/or amount of Sam68 is verified by monitoring levels of Sam68 transcript or protein produced by the target cell. In some embodiments, an increase of pro-apoptotic activity is verified by monitoring pro-apoptotic markers.

In some embodiments, increased expression and/or amount of Sam68 is verified by monitoring levels of Sam68. For example, in a single cell, a population of cells, or a biological sample, levels of Sam68 protein may be measured, levels of Sam68 transcript may be measured, or the sequence or presence of endogenous Sam68 gene may be identified. Levels of Sam68 protein may be measured by immunoblotting, ELISA, immunoprecipitation, flow cytometry, or immunohistochemistry. Levels of Sam68 transcript may be identified by northern blotting or rt-PCR. The presence of endogenous Sam68 gene may be identified by PCR, Southern blotting, or sequencing the Sam68 locus. The sequence of endogenous Sam68 may be inferred by sequencing at least one Sam68 locus in a cell or in a population of cells. An increase in Sam68 activity in a given cell may be inferred from an increase in Sam68 levels or Sam68 activity in a clone of that cell, in secretions from that cell, or in a population of cells from which that cell is derived. A detailed example of increasing Sam68 activity in cells with reduced Sam68 activity is described in Example 2, below.

In some embodiments, an increase of Sam68 is verified by monitoring levels of markers of Sam68 activity. Examples of markers of Sam68 activity include Sam68 transcript levels, Sam68 protein levels, ubiquitylated RIP, cleaved caspase 3, cleaved caspase 8, cleaved PARP, trypan blue exclusion of dead cells, neutral red assay, TUNEL staining, association of TRAF2 with TNFR, association of RIP with FADD, levels of A20 transcript or protein, as well as markers of activation of NF-kB signaling, which are discussed above.

Monitoring of Signal Transduction:

Surprisingly, Sam68 functions in TNF-dependent signaling, which affects NF-kB activation and activation of the extrinsic apoptotic pathway. As described in detail below, alteration in Sam68 activity and monitoring of Sam68 levels can be used to monitor TNF-dependent signaling, including NF-kB and apoptosis signaling.

In some embodiments, methods are provided for monitoring signal transduction activity in a mammalian cell. The NF-kB pathway and apoptosis can each be activated by either a TNF-dependent or TNF-independent pathway. There are situations where it would be beneficial to identify the mechanism by which the NF-kB pathway or apoptosis has been activated, for example when selecting a therapeutic, or predicting a certain clinical outcome. For example, if ectopic NF-kB signaling is activated in cancer cells via a mutation affecting the TNF-dependent branch of the pathway, it may be beneficial to prescribe a therapeutic that inhibits the TNF receptor. If a certain clinical outcome is associated with activation of the TNF-dependent apoptosis pathway in T-cells, it could be beneficial to determine whether this branch of the pathway is active. In some embodiments, inhibition of Sam68 can be used to determine which arm—TNF-dependent or TNF-independent—of the NF-kB or apoptosis pathway is active. This information can be used to select a particular course of treatment. By way of example only, NF-κB activation in a cell may be monitored by monitoring markers of NF-κB activation in the cell, a clone of the cell, a population of cells from which the cell was obtained, or a biological sample from the same organism from which the cell was derived to identify changes in one or more molecular marker of NF-κB activation. To determine the method of NF-κB activation in the cell, Sam68 is inhibited. In some embodiments, a control is provided by performing the same protocol on a cell known to have NF-κB activation, a cell known to be incapable of NF-κB activation, a cell in which Sam68 is not inhibited, or a cell in which Sam68 is known to be inhibited. If inhibition of Sam68 results in reduced NF-κB signaling activity compared to a control cell in which Sam68 is not inhibited, one skilled in the art will recognize that NF-κB was being activated in a TNF-dependent manner. If inhibition of Sam68 does not result in reduced NF-κB signaling activity compared to a control cell in which Sam68 is not inhibited, one skilled in the art will recognize that NF-B was being activated in a TNF-independent manner, or was being activated downstream of Sam68.

Apoptosis may be induced via a TNF-independent pathway—for example the fas-induced extrinsic apoptosis pathway or the stress-induced intrinsic apoptosis pathway—or the TNF-dependent extrinsic apoptosis pathway. In some embodiments, it is helpful to determine which branch of the pathway is active. For example, when selecting a therapeutic for a patient that targets a specific branch of the pathway, or when determining a clinical outcome associated with activation of a specific branch of the pathway. Markers of apoptosis may be monitored in the mammalian cell, a clone of the cell, a population of cells from which the cell was derived, or a biological sample from the same organism that the cells were derived from. In some embodiments, apoptosis is inhibited in cells that have been treated with the protein translation inhibitor cycloheximide. Since TNF stimulation rapidly activates NF-κB and induces synthesis of c-FLIP, a competitive inhibitor of caspase8 activation, inhibition of protein synthesis to block c-FLIP induction is a prerequisite to study TNF-induced death (Kreuz et al., 2001).

In some embodiments, a Sam68 inhibitor is administered to the cell or cells. The Sam68 inhibitor may be, for example, antisense RNA, dsRNA, siRNA, shRNA, decoy transcript, decoy peptide, or an antibody. In some embodiments, one or more markers of apoptosis are then monitored in the cell. In some embodiments, the cell is treated with an inhibitor of protein synthesis, for example cycloheximide. In some embodiments, a control is provided by performing the same protocol on a cell known to have activation of the extrinsic apoptotic pathway, a cell known to be incapable of activating the extrinsic apoptotic pathway, a cell in which Sam68 is not inhibited, or a cell in which Sam68 is known to be inhibited. If inhibition of Sam68 results in reduced activation of apoptosis compared to a control cell in which Sam68 was not inhibited, one skilled in the art will recognize that apoptosis was activated through the TNF-dependent branch of the extrinsic apoptotic pathway. If inhibition of Sam68 produces comparable apoptotic activation to a cell in which Sam68 was not inhibited, one skilled in the art will recognize that apoptosis was activated through a TNF-independent pathway.

Screening for Compounds that Affect TNF-Dependent Signaling

In some embodiments, methods are provided for screening for compounds that affect TNF-dependent NF-κB activation or activation of the TNF-dependent extrinsic apoptotic pathway, and are specific to the TNF-dependent pathway, or exert a substantially greater effect on the TNF-dependent pathway than on TNF-independent pathways. In some embodiments, the compounds are small molecule drug candidates. In some embodiments, the compounds are peptide mimetics. In some embodiments, the compounds are antibodies. In some embodiments, the compounds are agonists or antagonists of the TNF receptor. In some embodiments, compounds are identified that induce TNF-dependent NF-κB activation. Sam68+ cells and Sam68 knockout cells are each contacted with a candidate compound and one or more markers of NF-κB signaling are monitored in each type of cell. In some embodiments, the Sam68 knockout cell is a mouse fibroblast cell line comprising a knockout mutation in the Sam68 gene. The use and maintenance of Sam68 knockout mouse fibroblast cells is described in the examples below, including, for example, Example 1. Other Sam68 knockout cell lines can be generated or obtained using methods known in the art. In some embodiments, instead of Sam68 knockout cells, Sam68 knockdown cells are used. In some embodiments, instead of Sam68 knockout or knockdown cells, Sam68 is inhibited in Sam68+ cells using the methods described above. A person skilled in the art will recognize that a compound that induces TNF-dependent NF-κB activation will induce markers of NF-κB signaling in the Sam68+ cells, but not the Sam68 knockout cells. Markers of NF-κB signaling are described above.

In some embodiments, compounds are identified that induce TNF-independent NF-κB activation or activation of the TNF-dependent apoptosis pathway. In some embodiments, the compounds are small molecule drug candidates. In some embodiments, the compounds are peptide mimetics. In some embodiments, the compounds are antibodies. In some embodiments, the compounds are agonists or antagonists of the TNF receptor. In some embodiments, Sam68+ cells and Sam68 knockout cells are each contacted with a molecule and one or more markers of NF-κB activation are monitored in each type of cell. In some embodiments, instead of Sam68 knockout cells, Sam68 knockdown cells are used. In some embodiments, instead of Sam68 knockout or knockdown cells, Sam68 is inhibited in Sam68+ cells using the methods described above. A person skilled in the art will recognize that a drug candidate that induces TNF-independent NF-κB activation will induce markers of NF-κB activation in both the Sam68+ cells and the Sam68 knockout cells. Markers of NF-κB signaling are described above.

In some embodiments, compounds are identified that induce TNF-dependent activation of the extrinsic apoptotic pathway. Sam68+ cells and Sam68 knockout cells are each contacted with a drug candidate, and one or more markers of apoptotic activation are monitored in each type of cell. In some embodiments, cells are contacted with an inhibitor of protein synthesis, for example cycloheximide. A person skilled in the art will recognize that a drug candidate that induces TNF-dependent activation of the extrinsic apoptotic pathway manner will induce markers of apoptotic activation in both the Sam68+ cells and the Sam68 knockout cells. Markers of apoptotic activation are described above.

In some embodiments, drug candidates are identified that induce TNF-independent activation of the extrinsic apoptotic pathway. Sam68+ cells and Sam68 knockout cells are each contacted with a drug candidate, and one or more markers of apoptotic activation are monitored in each type of cell. In some embodiments, cells are contacted with an inhibitor of protein synthesis, for example cycloheximide. A person skilled in the art will recognize that a drug candidate that induces TNF-dependent activation of the extrinsic apoptotic pathway will induce markers of apoptotic activation in the Sam68+ cells, but not the Sam68 knockout cells. Markers of apoptotic activation are described above.

Kits

In some embodiments, kits are provided. Kits can include one or more of the following: wild-type cell lines, Sam68 knockout cell lines, shRNA directed against Sam68, siRNA directed against Sam68, TNF, IL-1, antibodies for monitoring changes in markers of NF-κB activation (for example, antibodies against phosphorylated IκB proteins, antibodies against NF-κB family transcription factors, antibodies against ubiquitylated RIP, antibodies against Sam68), primers for monitoring expression of NF-κB-dependent genes (SEQ ID NOs: 1-32 are examples of such primers, and methods are known in the art for designing additional primers targeted to NF-κB-dependent genes), cycloheximide, antibodies for monitoring markers of apoptotic activation (for example, antibodies against cleaved Caspase 3, cleaved caspase 8, or cleaved PARP), reagents for monitoring activation of the pro-apoptotic pathway (for example trypan blue, neutral red, and TUNEL), packaging, and instructions.

EXAMPLES

In the following examples, Sam68 knock out and control wild type Mouse Embryonic Fibroblast cells (MEF) were provided by Dr. Stephane Richard, McGill University, Canada. Mouse embryonic fibroblasts (MEF), 293-T and HeLa cells were grown in DMEM complete media (100 U/ml penicillin/streptomycin, 4 mM L-glutamine and 10% fetal bovine serum). Total cell lysates were prepared in the following manner: cells were lysed on ice for 30 minutes in the lysis buffer (11 mM Sodium phosphate pH 7.4, 150 mM NaCl, 0.1% SDS, 0.5% Sodium deoxycholate, 1% Triton X-100 and 1× complete protease inhibitor cocktail).

Example 1

Knocking Out Sam68 Impairs TNF-Dependent Signaling in Mammalian Cells

Figure 1:
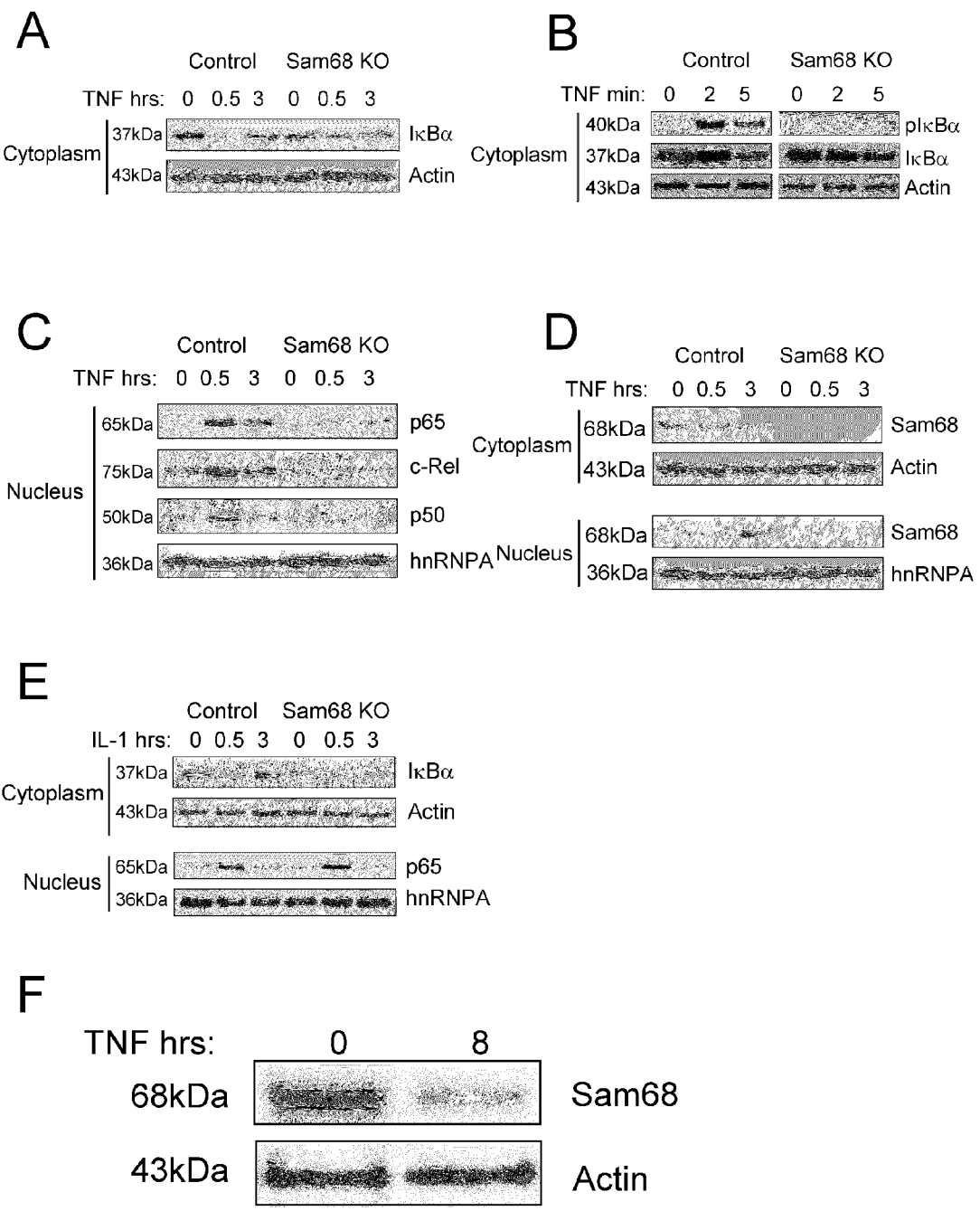
FIG. 1 illustrates that TNF induced NF-κB activation is attenuated in Sam68 knockout cells, while the IL-1 pathway is not affected. (A) Control and Sam68 knockout fibroblasts were treated with TNF for the indicated times and cytoplasmic extracts were immunoblotted with anti-IκBα antibody. (B) Total lysates from control and Sam68 knockout cells were immunoblotted for phosphorylated IκBα and IκBα. (C) Nuclear extracts from (A) were immunoblotted for p65, c-Rel, p50. (D) Cytoplasmic and nuclear extracts from (A) and (C) were immunoblotted for Sam68. (A), (C) and (D) were performed with lysates from same experiment. (E) IL-1 induced NF-κB activation is normal in Sam68 KO cells. Cells were treated with 100 ng/ml recombinant human IL-1 beta for the indicated times. Cytoplasmic and nuclear extracts were immunoblotted with anti-IκBα and anti-p65 antibodies. In all the above blots actin and hnRNPA were used as cytoplasmic and nuclear loading controls respectively. (F) Jurkat cells were treated with TNF for the indicated time points and cytoplasmic extracts were immunoblotted using Sam68 and actin antibodies.

Prolonged TNF stimulation of Jurkat cells caused a dramatic reduction in the cytoplasmic levels of a protein called Sam68 (FIG. 1F). Mouse embryonic fibroblasts also showed decreased Sam68 levels in the cytoplasm following long-time TNF stimulation (FIG. 1D). The decrease in cytoplasmic Sam68 levels was paralleled by a corresponding increase in its nuclear level indicating that Sam68 is a TNF responsive protein (FIG. 1D).

Wild type control and Sam68 knockout fibroblast cells were treated with TNF (Recombinant human TNFα from Peprotech), and IκBα degradation and nuclear translocation of NF-κB protein were used to monitor the activation of their NF-κB pathway (IκBα antibody was from Santa Cruz Biotechnology; assessment of NF-κB nuclear translocation, cytoplasmic and nuclear extracts were prepared as described by Schreiber et al., 1989).

Deficiency of Sam68 resulted in greatly reduced TNF-induced IκBα degradation in the cytoplasm (FIG. 1A). Moreover, phosphorylation of IκBα was analyzed following short-time TNF stimulation of the cells (phosphorylated IκBα antibody was from Cell Signaling Technology). Sam68 knockout cells exhibited almost complete blockage of IκBα phosphorylation in (FIG. 1B). In addition to the decreased IκBα phosphorylation and degradation, Sam68 deficiency also caused a dramatic reduction in nuclear translocation of p65, c-Rel and p50 subunits of NF-κB (FIG. 1C) (p65, c-Rel, and p50 antibodies were from Santa Cruz Biotechnology). Additionally, Sam68 knockout cells showed decreased levels of IκBα protein in the cytoplasm (compare FIG. 1A lane 1 and lane 4). The above results are consistent with reduced NF-κB signaling activity in the Sam68 knockout cells as compared to wild type cells.

The Sam68 knockout fibroblast cells were treated with IL-1β (R&D Systems), another proinflammatory cytokine. IL-1β induced NF-κB activation remained intact in these cells, as indicated by IκBα degradation and nuclear translocation of p65 (FIG. 1E). Thus, the NF-κB activation pathway is functional in these Sam68 knockout cells, while Sam68 activity is specifically related to TNF signaling.

Figure 2:
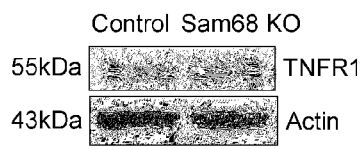
FIG. 2 illustrates TNF induced JNK and ERK activation does not require Sam68. (A) and (B) Sam68 knockout cells expressed similar levels of TNF receptor as wild type cells. (A) Cells lysates were immunoblotted using anti-TNFR antibody. (B) Cells were analyzed by flow cytometry for surface expression of TNFR using PE conjugated anti-mouse TNFR antibody. Mean Fluorescence Intensity (MFI) of TNFR signal from control and Sam68 knockout cells (left panel). Filled peak in histogram overlay represents unstained control cells and open peak represents anti-TNFR stained cells (right panels). (C) and (D) TNF induced JNK and ERK activation is enhanced in Sam68 knockout cells. (C) Cytoplasmic extracts from FIG. 1 (A) were immunoblotted using phosphorylated JNK and total JNK antibodies. (D) Cells were starved overnight in serum free medium and then treated with TNF for indicated times. Cell lysates were immunoblotted using phosphorylated ERK and total ERK antibodies. Actin was used as loading control.
Figure 2:
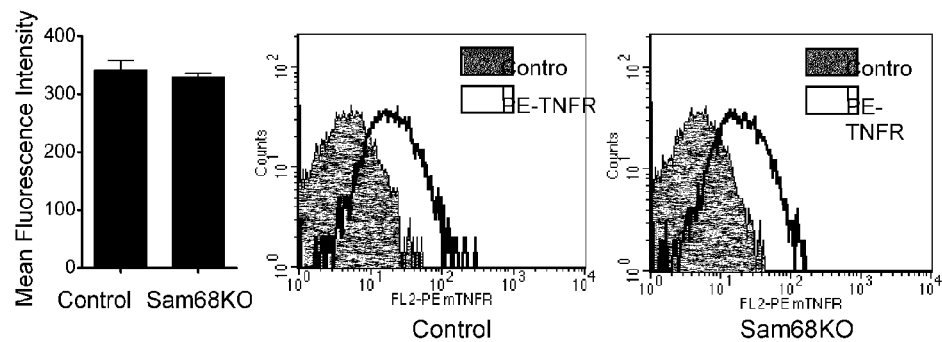
Figure 2:
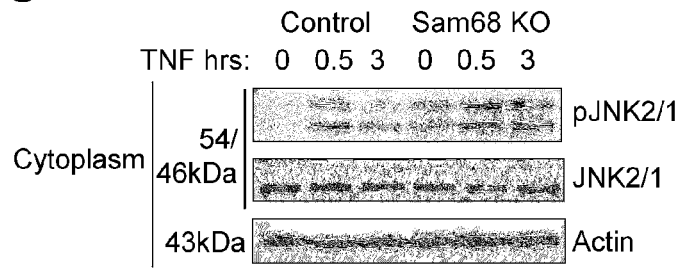
Figure 2:
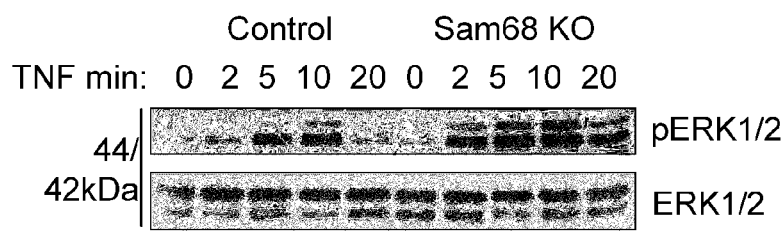

The observed reductions in NF-κB signaling in Sam68 knockout cells were not due to a difference in the expression of TNF receptor in these cells. Total cell lysate analysis by immunoblotting confirmed that the TNF receptor is expressed at similar levels in both the wild-type control and Sam68 knockout cells (FIG. 2A). Flow cytometry confirmed that surface expression of TNF was comparable in wild-type control and Sam68 knockout cells (FIG. 2B).

Example 2

Sam68 Deficiency Blocks TNF Induced NF-κB Dependent Gene Expression

NF-κB dependent gene expression was assessed in Sam68 knockout cells by quantitative RT-PCR (Hao and Baltimore, 2009. Nature immunology 10, 281-288.). Cells were stimulated with TNF (Recombinant human TNFα was from Peprotech) for two time points: 30 minutes to capture early genes and 3 hours for the late genes. Quantitative RT-PCR was performed as follows: DNA free RNA was prepared using the RNeasy Mini Kit according to the manufacturer's instructions (Qiagen). cDNA was synthesized from 0.5-1.0 µg total RNA using random hexamers (Promega) and Superscript III reverse transcriptase first-strand synthesis kit (Invitrogen). Quantitative real time PCR using cDNA corresponding to 10-20 ng of total RNA was performed using SYBR GREEN PCR Master Mix (Kapa biosystems) in a Real-Time PCR machine (Realplex, Eppendorf). The results obtained for individual genes were normalized to the ribosomal protein Rpl32. The primers used for PCR were designed from Primer Bank (http://pga.mgh.harvard.edu/primerbank/index.html) or Oligoperfect (http://tools.invitrogen.com/content.cfm?pageid=9716) and their sequences are given in Table 1.

Figure 3:
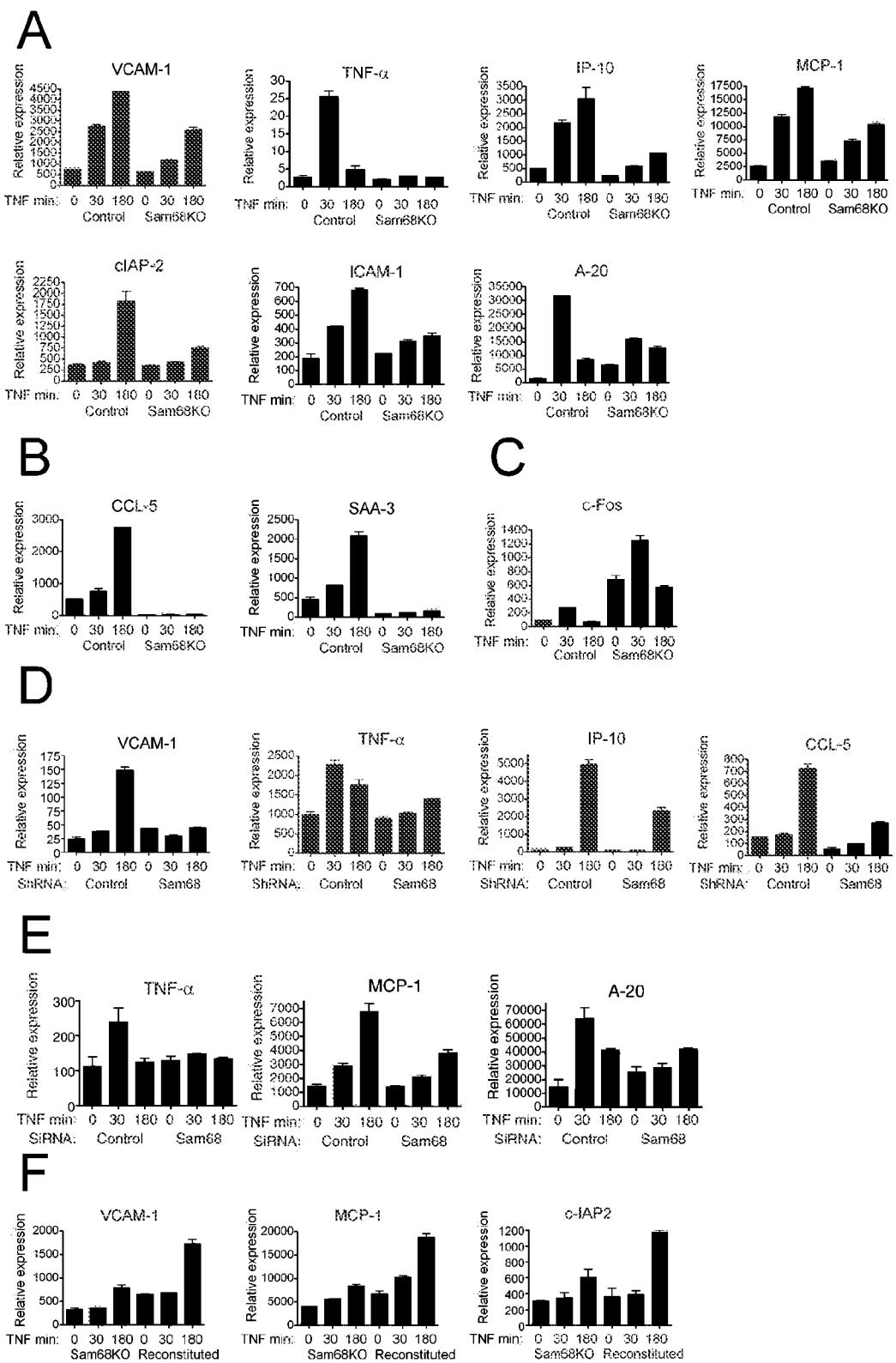
FIG. 3 illustrates TNF induced NF-κB dependent gene expression is greatly reduced in Sam68 knockout cells. (A) Control and Sam68 knockout cells were treated with 10 ng/ml of TNF for the indicated times. RNA was prepared from three independent experiments. Quantitative real time PCR was performed and relative abundance of each transcript was calculated with respect to the expression of ribosomal protein L32. Quantitative PCR primer pairs are described in Table 1. Statistical significance was determined by two-tailed unpaired student's t test. All the represented genes showed a P value of <0.05. (B) Expression of CCL-5 and SAA-3 was quantified as above. (C) Expression of JNK dependent gene c-Fos was quantified as above. (D) Control and Sam68 suppressed MEF cells were treated and gene expression was studied as above. (E) Sam68 KO cells and Sam68 KO cells reconstituted with FLAG-Sam68 (F) were treated, and gene expression was studied as above. (F) Sam68 knock out cells and Sam68 knockout cells reconstituted with FLAG tagged wild type mouse Sam68 were treated and gene expression was studied as in (A).

Overall expression of the NF-κB target genes was substantially reduced in Sam68 knockout cells as compared to the wild type cells. Different NF-κB target genes studied showed different degree of requirement of Sam68 for their expression. Expression of some genes, for example TNFα and IP-10, was reduced up to 5-fold in Sam68 knockout cells. Expression of several other genes, for example VCAM-1, c-IAP2, A20, ICAM-1 and MCP-1 was reduced by around 2 fold in Sam68 knockout cells. Sam68 deficiency by itself did not decrease the basal expression level of these genes, and the observed reduction was entirely due to interference in TNF signaling (FIG. 3A). Some NF-κB target genes, for example CCL5 and SAA3 showed total dependence on Sam68 for their expression at both their basal and TNF induced levels and they were completely blocked in Sam68 knockout cells (FIG. 3B).

The expression of a JNK dependent gene, c-Fos (Ventura et al., 2003. Mol Cell Biol 23, 2871-2882.), was also monitored in Sam68 knockout cells. Basal c-Fos expression was elevated in Sam68 knockout cells and TNF stimulation resulted in further increase in c-Fos expression (FIG. 3C).

Figure 4:
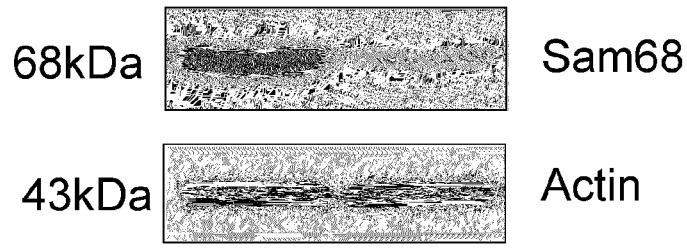
FIG. 4 illustrates shRNA or siRNA mediated suppression of Sam68 compromise TNF induced gene expression. (A) HeLa cells were transduced with either control or shRNA expressing lentivirus and puromycin resistant cells were analyzed for Sam68 expression by immunoblotting. (B) MEF were transfected with either control or siRNA Sam68 and 48 hours later analyzed by immunoblotting for Sam68 expression. Actin was used as loading control. (C) MEF cells transfected with control or Sam68 siRNA were treated with TNF as indicated and TNF expression was estimated by quantitative real time PCR.
Figure 4:
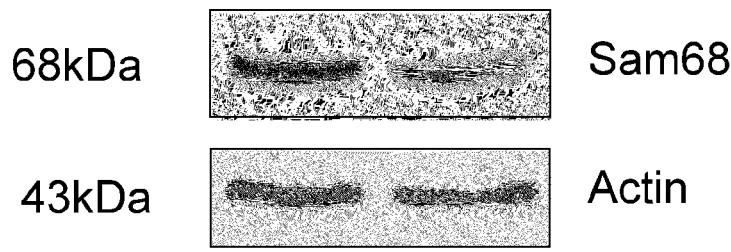
Figure 4:
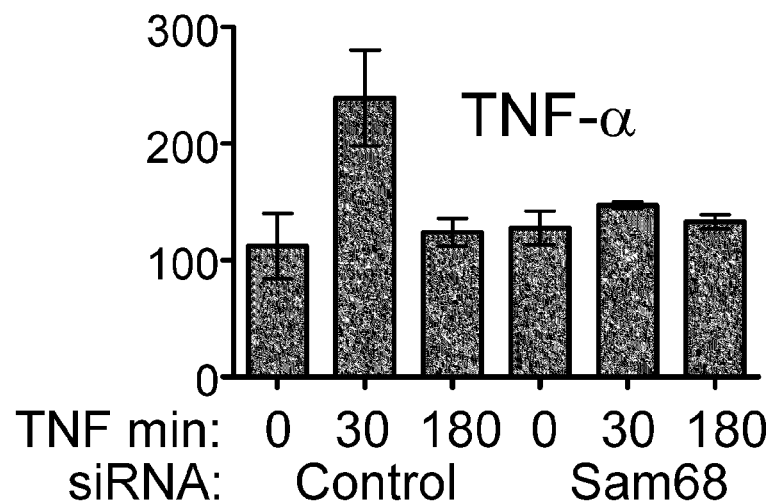

Sam68 expression was suppressed in human HeLa cells using lentiviral shRNA against human Sam68 (Santa Cruz), and transduced cells were selected using 2 µg/ml puromycin. Cells transduced with Sam68 shRNA showed approximately 70% suppression of Sam68 protein level compared to the control shRNA transduced cells (FIG. 4A). TNF-induced HeLa cells with reduced Sam68 expression, and showed diminished expression of NF-κB dependent gene expression when compared to TNF-induced wild-type HeLa cells (FIG. 3D).

Sam68 siRNA and siCONTROL nontargeting siRNAs was obtained from Dharmacon. siRNA mediated suppression of Sam68 was performed in mouse fibroblasts by transfecting these cells using Lonza nucleofector device. Even though the efficiency of Sam68 suppression in fibroblasts was only 40% (FIG. 4B), a decrease in the induction of TNFα expression was observed (FIG. 4C).

Figure 5:
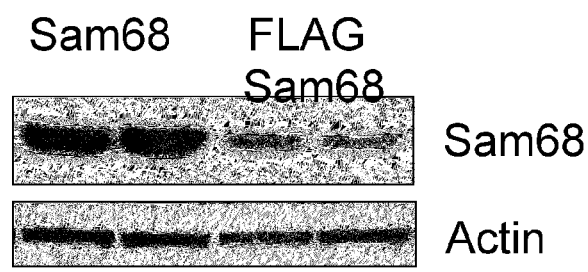
FIG. 5 illustrates Sam68 reconstitution of Sam68 knockout cells rescue TNF induced gene expression. Sam68 knockout cells were nucleofected with a plasmid encoding FLAG-Sam68 and Sam68 expression in a single cell derived clone was analyzed by immunoblotting. Samples were analyzed in duplicates.

Sam68 expression was reconstituted in the Sam68 knockout fibroblast cells by using a FLAG-tagged wildtype Sam68 cDNA to express Sam68 in these cells. Mouse Sam68 cDNA was cloned into pIRES.Puro vector (Invitrogen) to generate pIRES.Puro-FLAGSam68. Introducing FLAG-Sam68 cDNA by lentiviral transduction, yielded cells that expressed only 25-30% of the transduced protein. In order to get higher levels of FLAG-Sam68 reconstitution in Sam68 knockout cells, fibroblasts were transfected by nucleofection. Nucleofection was performed using nucleofector device in MEF solution 1 and program A023 following manufacturer's instruction (Lonza). Several single cell-derived clones were screened for FLAG-Sam68 expression (Anti-FLAG antibody was from Sigma) and some clones expressed up to 50% of the transduced protein (FIG. 5). Although partial, the ectopic expression Sam68 in these Sam68 knockout cells did increase the expression of NF-κB target genes (FIG. 3F).

Example 3

TNF-Independent JNK and ERK Activation is not Blocked in Sam68 Knockout Cells:

In addition to NF-κB, TNF is also reported to activate mitogen-activated protein kinases (MAPKs), including the extracellular signal-regulated kinase (ERK) and c-Jun N-terminal kinase (JNK) pathways (Karin and Gallagher, 2009. Immunological reviews 228, 225-240.). Activation of JNK and ERK was monitored by immunoblotting following TNF stimulation in wildtype and Sam68 knockout cells. Antibodies against JNK and ERK were from Santa Cruz Biotechnology.

Unlike NF-κB, JNK activation was not reduced in Sam68 knockout cells. Rather, the level of phosphorylated JNK was increased above basal level and sustained even at 3 hours post TNF stimulation (FIG. 2C).

ERK activation was monitored in serum-starved cells to minimize high basal phosphorylation of ERK. Like JNK pathway, activation of ERK by TNF was also intact and enhanced as indicated by the augmented phosphorylation of ERK in Sam68 knockout cells (FIG. 2D).

Example 4

Sam68 Deficiency Blocks TNF Induced Apoptosis

TNF stimulation has been reported to activate proinflammatory and cell survival as well as apoptotic pathways (Chen and Goeddel, 2002. Science 296, 1634-1635). While the survival pathway mainly relies on activation of NF-κB (Baker and Reddy, 1998. Oncogene 17, 3261-3270.), apoptosis depends on activation of caspases (Varfolomeev et al., 1998. Immunity 9, 267-276.) (Wang et al., 2008. Cell 133, 693-703).

Figure 6:
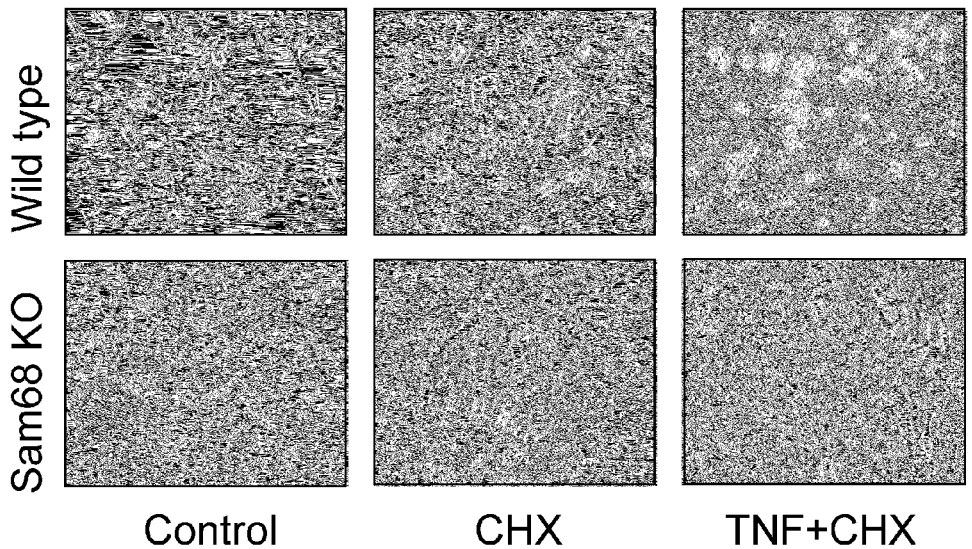
FIG. 6 illustrates Sam68 is required for cycloheximide induced TNF dependent apoptosis (A) Control and Sam68 knockout cells were seeded in 6 well plates and treated with either cycloheximide (5 μg/ml) alone or cycloheximide and TNF (100 ng/ml) for 6 hours. Cells were visually examined on a Nikon Diaphot 300 phase contrast microscope at 200× final magnification and photographed using a SPOT digital camera and software. Data represented is one out of five independent experiments performed. Cell death was quantified either by (B) counting absolute cell numbers following trypan blue exclusion of dead cells or by (C) neutral red assay. (D) Cells were treated as in (A) and harvested just before the appearance of apoptotic morphology by 2.5-3.5 hours. Cell lysates were immunoblotted using anti-PARP and anti-cleaved caspase3 antibodies. (E) Control and Sam68 suppressed HeLa cells were treated as above for 8 hours and cell death was quantified by counting absolute cell numbers following trypan blue exclusion of dead cells.
Figure 6:
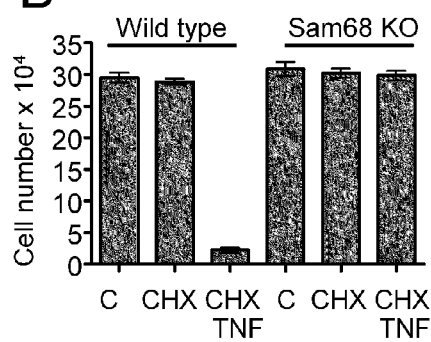
Figure 6:
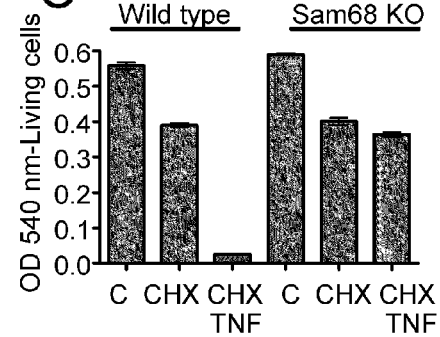
Figure 6:
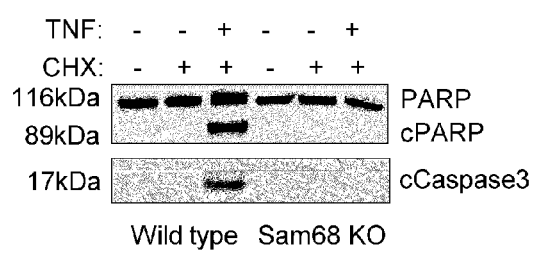
Figure 6:
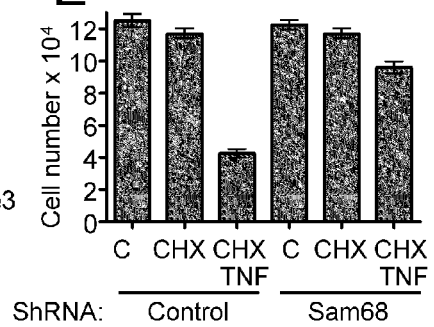

Wild-type and Sam68 knockout fibroblasts were treated with TNF in the presence of protein translation inhibitor cycloheximide (CHX) (Sigma). Since TNF stimulation rapidly activates NF-κB and induces synthesis of c-FLIP, a competitive inhibitor of caspase8 activation, inhibition of protein synthesis to block c-FLIP induction is a prerequisite to study TNF-induced death (Kreuz et al., 2001). Wild type cells underwent apoptosis 3-4 hours after stimulation with TNF, while no death was observed in Sam68 knockout cells up to 12 hours after stimulation. Cells were analyzed by microscopy, and while wild-type cells treated with TNF and cycloheximide underwent morphological changes consistent with apoptosis, Sam68 knockout cells did not (FIG. 6A). Cells were analyzed by trypan blue exclusion staining for the absolute number of living cells, and while the cell count of wild-type cells treated with TNF and cycloheximide decreased more than ten-fold, there was no observable decrease in the cell count of Sam68 knockout cells treated with TNF and cycloheximide (FIG. 6B). Cells death was quantified by neutral red uptake assay, and wild-type cells treated with TNF and cycloheximide exhibited a striking decrease in the quantity of living cells, Sam68 knockout cells treated with TNF and cycloheximide exhibited little decrease in the quantity of living cells (FIG. 6C). Cell extracts were assayed for caspase3 activation and cleavage of the caspase substrate, PARP (antibody against PARP was from Santa Cruz Biotechnology; antibody against cleaved caspase3 was from Cell Signaling Technology). Immunoblotting showed cleaved caspase3 and cleaved PARP in the wildtype cells treated with TNF and cycloheximide, while no caspase3 activation or PARP cleavage was observed in Sam68 knockout cells (FIG. 6D). Additionally, Sam68 expression was suppressed in HeLa cells by expressing shRNA Sam68 in these cells: HeLa cells were transduced with lentivirus expressing shRNA against human Sam68 (Santa Cruz) and selected in 2 µg/ml Puromycin. Sam68-suppressed HeLa cells showed resistance to TNF plus cycloheximide induced-apoptosis: while treating wild-type HeLa cells with TNF and cycloheximide reduced the number of cells nearly three-fold, there was no such reduction for Sam68-suppressed cells treated with TNF and cycloheximide (FIG. 6E).

Sam68 is not Required for Fas Induced Extrinsic or Stress Induced Intrinsic Pathway of Apoptosis Apoptosis occurs either by extrinsic pathway or by intrinsic pathway. In the extrinsic pathway, the apoptosis is initiated by a death inducing ligand binding to its cognate receptor in the membrane followed by recruitment, aggregation and activation of caspases (Park et al., 2007). In the intrinsic pathway, non-receptor cellular stress like DNA damage or oxidative stress causes increase in mitochondrial permeability, which leads to release of pro-apoptotic factors in to the cytosol that activate caspases (Brenner and Mak, 2009. Current opinion in cell biology 21, 871-877.).

Figure 7:
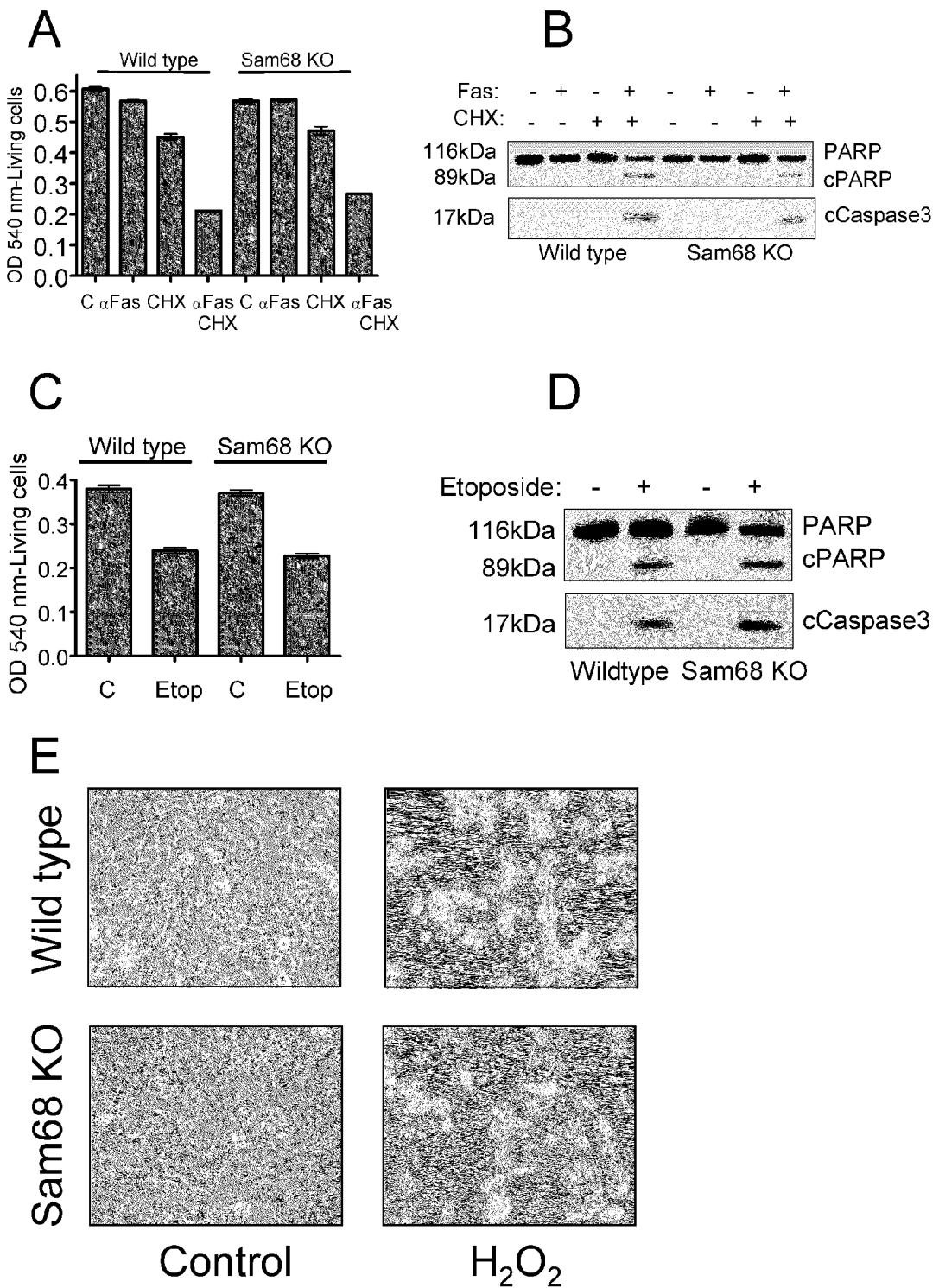
FIG. 7 illustrates Sam68 is not required for Fas induced or genotoxic stress induced apoptosis. (A) Control and Sam68 knockout cells were seeded in 6 well plates and treated in triplicates with either cycloheximide (5 μg/ml) alone or cycloheximide and anti-Fas antibody (2 μg/ml) for 12 hours. Cell death was quantified by Neutral red assay. Data represented is one out of three independent experiments performed. (B) Cells were treated as in (A) and harvested just before the appearance of apoptotic morphology by 6-7 hours. Cell lysates were immunoblotted using anti-PARP and anti-cleaved caspase3 antibodies. (C) Cells were treated with Etoposide (200 μM) for 24 hours and cell death was quantified by Neutral red assay. (D) Cells were treated as in (C) and harvested by 12 hours. Cell lysates were immunoblotted using anti-PARP and anti-cleaved caspase3 antibodies. (E) Cells were treated with hydrogen peroxide (100 μM) for 24 hours and visually examined as in FIG. 6 (A).

Fas is a prototypic death receptor that induce apoptosis by the extrinsic pathway (Krammer, 2000. Nature 407, 789-795.) (Wallach et al., 1999. Annual review of immunology 17, 331-367.). Wildtype and Sam68 knockout cells were stimulated with agonistic anti-Fas antibody (BD Biosciences) and cycloheximide (Sigma). Fas stimulation induced apoptosis of both wildtype and Sam68 knockout cells, as measured by optical density of living cells at 540 nm (FIG. 7A). Immunoblotting analysis of activation of caspase3 and cleavage of PARP (antibody against PARP was from Santa Cruz Biotechnology; antibody against cleaved caspase3 was from Cell Signaling Technology) following anti-Fas antibody plus cycloheximide stimulation showed that both proteins were cleaved in wildtype and Sam68 knockout cells (FIG. 7B). However, the Fas-induced apoptosis and cleavage of caspase3 and PARP were slightly reduced in the Sam68 knockout cells compared to the wildtype cells. The results in this example are consistent with the conclusion that extrinsic apoptotic pathway as well as caspase activation is intact in Sam68 knockout cells and Sam68 activity is specific for TNF signaling.

Cell death via the intrinsic pathway of apoptosis can be induced by genotoxic and oxidative stress (Roos and Kaina, 2006. Trends in molecular medicine 12, 440-450.) (Dumont et al., 1999. Oncogene 18, 747-757.). Etoposide (Sigma), an anti-neoplastic chemical that inhibits topoisomerase I (Mizumoto et al., 1994. Molecular pharmacology 46, 890-895.), was used to induce DNA damage. Etoposide induced apoptosis to a similar extent in both wildtype and Sam68 knockout cells, as measured by optical density of living cells at 540 nm (FIG. 7C). Moreover, etoposide resulted in similar levels of activation of caspase3 and PARP cleavage in both wild-type and Sam68 knockout cells (FIG. 7D). Oxidative stress was induced by hydrogen peroxide, and caused death induction in both wildtype and Sam68 knockout cells, as measured by cell morphology (FIG. 7E). The results in this example demonstrate that DNA damage and oxidative stress-induced apoptosis does not require Sam68 and emphasize the unique dependence of TNF signaling on Sam68 for inducing apoptosis.

Example 5

Sam68 is Part of Complex I of TNF Receptor Signaling and Knocking out Sam68 Blocks RIP Ubiquitylation and Kinase Activation in the NF-κB Pathway:

There exist two distinct signaling complexes that associate with the TNF receptor, one dedicated to NF-κB activation (complex I) and the other for apoptosis (complex II) respectively (Micheau and Tschopp, 2003. Cell 114, 181-190.).

Figure 8:
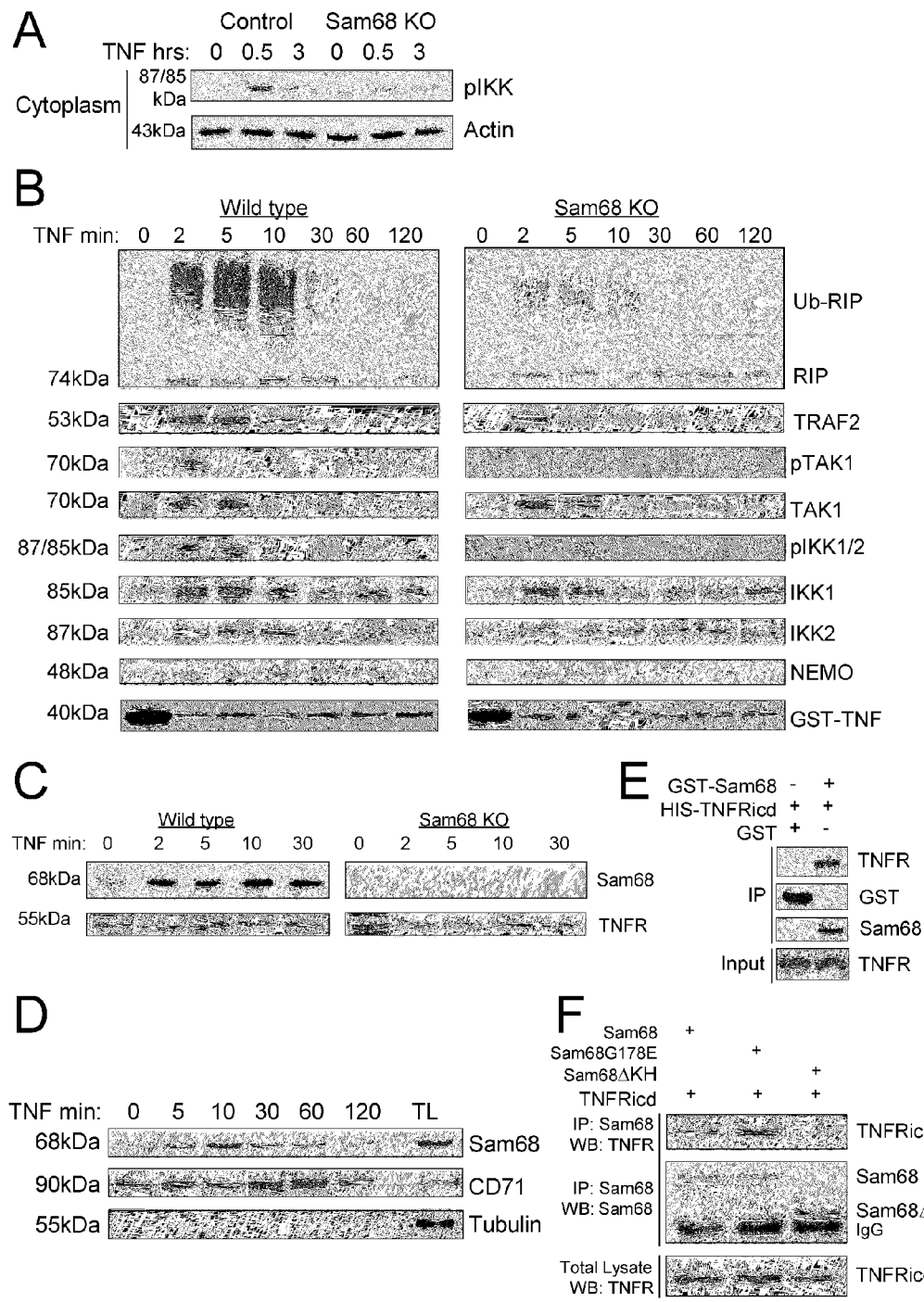
FIG. 8 illustrates Sam68 is required for signaling from complex I of TNF receptor. (A) Control and Sam68 knockout fibroblasts were treated with TNF for the indicated times and cytoplasmic extracts were immunoblotted with anti-phospho IKK antibody. (B) Kinetic analysis of recruitment of signaling molecules to TNF receptor. Wild type and Sam68KO cells were treated with GST-TNF for indicated time points and the receptor-associated complex was immunoprecipitated through the GST tag using glutathione sepharose beads. The data presented is representative of seven independent experiments. (C) Cells were treated and immunoprecipitated as above and Sam68 recruitment was assessed by immunoblotting. TNF receptor shows the uniformity of immunoprecipitation. (D) Sam68 is present in association with cell membrane. Wild type fibroblasts were treated with TNF as above for the indicated time points. Membrane fractions were immunoblotted with anti-Sam68 and anti-CD71 antibodies. Total cell lysate was loaded as a control for protein expression. Tubulin was used as a control for the purity of membrane fraction. (E, F) Sam68 binds to TNF receptor through its KH domain. (E) In vitro binding assay of recombinant GST-tagged mouse Sam68 and HIS-tagged human TNF receptor intracellular domain (TNFRicd). (F) HeLa cells transduced with shRNA Sam68 were transiently transfected with either wild type Sam68 or Sam68ΔKH and Flag tagged TNFRicd. Sam68 immunoprecipitate was immunoblotted for co-precipitating TNFRicd (top panel) and Sam68 (middle panel). The bottom panel shows the expression level of TNFRicd in the cell lysate.

Immunoblotting was performed on extracts from Sam68 knockout cells, using antibodies against phosphorylated IKK1/2 (Cell Signaling Technology), and showed that IKK phosphorylation was greatly decreased in Sam68 knockout cells (FIG. 8A).

Immunoprecipitation was performed on GST-TNF in cell extracts in the following manner: Cells were treated with GST-TNF (1 µg/ml) for various time points. For time '0', 100 ng/ml GST-TNF was added to the untreated cell lysate. The receptor-associated complex was immunoprecipitated through the GST tag using glutathione sepharose beads (GE healthcare) for 3-4 hours at 4° C. Antibodies were as follows: antibodies against TRAF2, TAK1, IKK1, and NEMO (Santa Cruz Biotechnology), antibodies against Rip (BD Biosciences), phosphorylated TAK1 and phosphorylated IKK1/2 (Cell Signaling Technology), TAK1 (Santa Cruz Biotechnology). The immunoprecipitation showed that while the amount of RIP recruited to the TNF receptor complex was comparable in both wildtype and Sam68 knockout cells, RIP ubiquitylation was greatly decreased in Sam68 knockout cells (FIG. 8B). TRAF2 has been suggested to be essential for RIP ubiquitylation (Ea et al., 2006. Mol Cell 22, 245-257.) (Alvarez, 2010. Nature 465, 1084-1088) (Wertz et al., 2004. Nature 430, 694-699.) (Lee et al., 2004. The Journal of biological chemistry 279, 33185-33191.). A similar amount of recruited TRAF2 was seen in wildtype and Sam68 knockout cells at 2 minutes after TNF stimulation (FIG. 8B). However, TRAF2 dissociated rapidly from the receptor complex in Sam68 knockout cells, but did not dissociate rapidly in wild-type cells (FIG. 8B). Additionally, phosphorylation of TAK1 and IKK1/IKK2 was detected in wild-type cells, but was not detectable in Sam68 knockout cells (FIG. 8B). However, recruitment of TAK1 or the signalosome complex (IKK1, IKK2 and NEMO) to the TNF receptor was not inhibited in Sam68 knockout cells (FIG. 8B).

Immunoprecipitation of GST-TNF using the protocol described above also showed that Sam68 is part of the TNF receptor complex: Sam68 was bound to the TNF receptor at a low level in unstimulated cells and its recruitment steadily increased with TNF stimulation (FIG. 8C). The uniformity of the immunoprecipitation was confirmed by immunoblotting for TNF receptor (FIG. 8C bottom panel).

In vitro binding assays were performed, and identified binding between bacterially produced recombinant GST-tagged Sam68 and the HIS-tagged TNF receptor intracellular domain (TNFRicd) (FIG. 8E). Additionally, a deletion mutant of Sam68 lacking the KH domain (amino acids 157-256) and a point mutant (G178E) were generated. The KH domain was required for Sam68 binding to the TNF receptor (FIG. 8F). To generate pIRES.Puro-Sam68ΔKH (amino acids 157-256 deleted), the corresponding cDNA was subcloned from pcDNA3 HA-Sam68ΔKH (Addgene). HA tagged wild-type mouse Sam68 was cloned in pcDNA3 vector (Invitrogen). The intracellular domain of human TNF receptor (amino acids 235-455) with an N-terminal FLAG tag was cloned into pcDNA3 vector (Invitrogen) to generate FLAG-TNFRicd. The in vitro binding assays were performed in the following manner: Bacterial expression of a GST-fusion protein of Sam68 done according to the GST Gene Fusion System protocol of the manufacturer (Pharmacia Biotech). Sam68 was expressed in BL21-GOLD cells (Agilent Technologies, Stratagene). HIS-TNFRicd was expressed in BL-21 (DE3)pLysS cells (Novagen) and purified using nickel affinity chromatography. Induction of all proteins was carried out at OD 600 of 0.4-0.5 with 0.1 mM isopropyl-β-D-thio-galactopyranoside for 4 h at 25° C. Binding of Sam68 to the TNF receptor was also detected by transient expression in HeLa cells.

Figure 11:
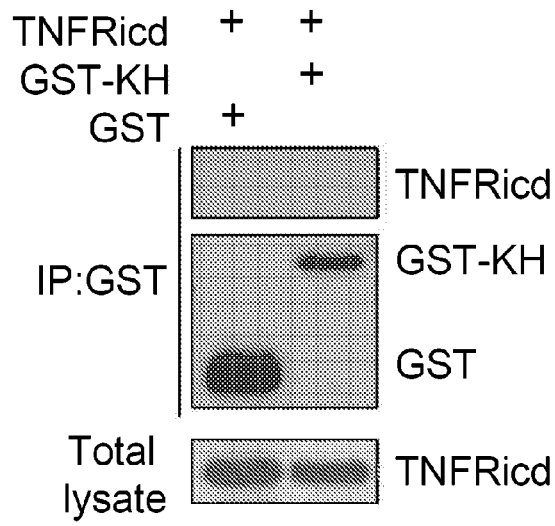
FIG. 11 illustrates TNF stimulation does not induce Sam68 phosphorylation. (A) 293T cells were transfected with the indicated plasmids and GST-KH domain was precipitated using glutathione beads. Anti-TNFR and anti-GST antibodies were used to detect TNFRicd and GST-KH expression respectively. TNF stimulation does not induce Sam68 phosphorylation. (B) MEF cells were serum starved overnight and then treated with 20% fetal bovine serum for the indicated time points. Sam68 was immunoprecipitated and immunoblotted using anti-phospho tyrosine antibody (top panel) and Sam68 antibody (bottom panel). pSam68 represents phosphorylated Sam68. (C) In vivo radio-phosphate labeling. MEF cells were radiolabeled with [32P]-orthophosphate and treated with TNF for the indicated time points. Sam68 was immunoprecipitated and incorporation of radioactive phosphate was assessed by autoradiography (top panel). Immunoblotting was performed to detect Sam68 levels in the samples (middle panel) and IκBα degradation (bottom panel) to confirm efficiency of TNF stimulation.
Figure 11:
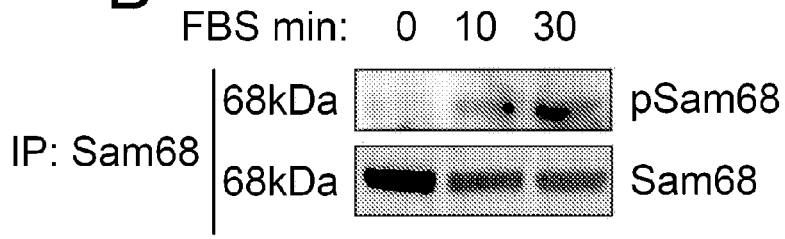
Figure 11:
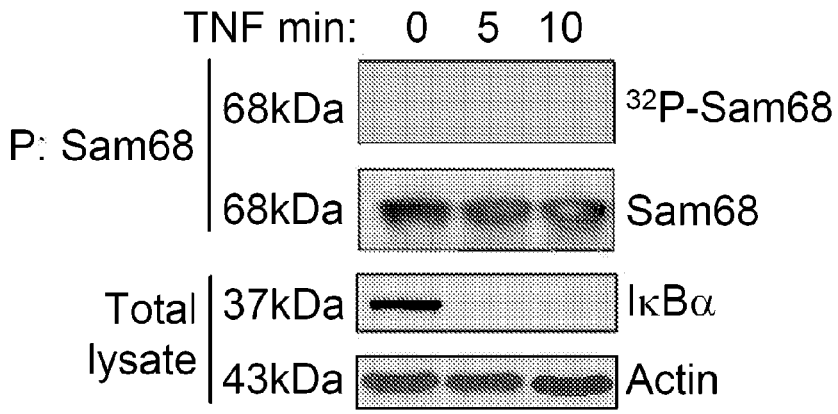

However, the KH domain, when expressed alone, was unable to bind TNFR, suggesting that it is a structural component required for binding and not the binding domain itself (FIG. 11A).

Figure 10:
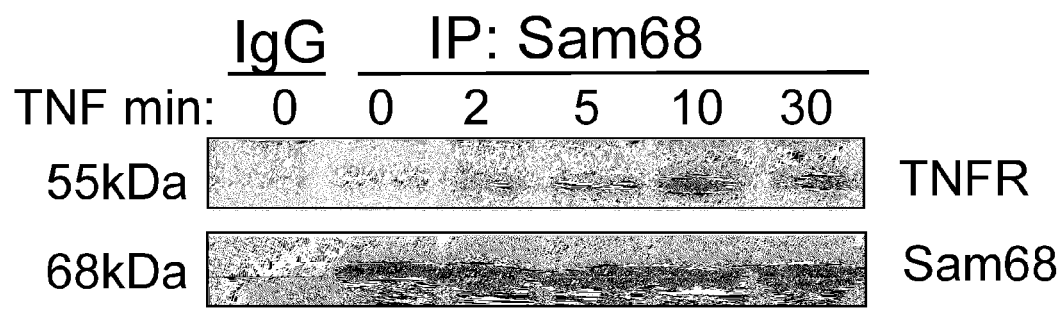
FIG. 10 illustrates Sam68 is recruited to TNF receptor. 20×10$^6$ wild type MEF cells were treated with TNF as indicated and Sam68 was immunoprecipitated using anti-Ssam68 antibody. Co-precipitation of TNF receptor was detected by immunoblotting using anti-TNFR antibody. Immunoprecipitation using rabbit-IgG was used as a control for non-specific binding. Bottom panel shows amount of Sam68 in the immunoprecipitate.

In HeLa cells, stimulation with TNF induced the association of Sam68 with the TNF receptor, along with ubiquitylated RIP and TRAF2 (FIG. 9E). Reverse immunoprecipitation of TNF receptor was performed through endogenous Sam68. 20-25×10$^6$ control and treated cells were lysed in a rotator at 4° C. for 30 minutes in the lysis buffer (1.0% Triton-X100, 20 mM HEPES (pH 7.6), 150 mM NaCl, 1 mM EDTA, 10% glycerol and complete protease inhibitor cocktail). The immunoprecipitates were washed thrice with the lysis buffer and boiled with LDS sample buffer (Invitrogen). Samples with the endogenous protein complexes were resolved in Novex 4-12% Bis-Tris gels (Invitrogen) and transferred to nitrocellulose membrane, probed using relevant antibodies and detected using the SuperSignal West Pico or West Femto Chemiluminescent Substrate System (Pierce). Detection of proteins in the immunoprecipitates with molecular weight close to the denatured heavy and light chains of immunoglobulins (50 kDa and 25 kDa respectively) was performed using native IgG detection reagent (Pierce). The reverse immunoprecipitations with Sam68 demonstrated a ligand-dependent increase in Sam68 binding to the TNF receptor (FIG. 10). Additionally, membrane fractionation was performed on cells treated with TNF. The isolated membrane fractions were free of cytoplasmic contamination as shown by the lack of tubulin, and these fractions contained Sam68 and the membrane marker transferring receptor (CD71) (FIG. 8D). There was a TNF-induced modulation of Sam68 protein level in the membrane fraction (FIG. 8D).

The binding of Sam68 to RIP was examined using an in vitro binding assay. It was observed that Sam68 and RIP bind directly to each other (FIG. 15C). Moreover, overexpressed RIP was specifically immunoprecipitated through endogenous Sam68 in 293T cells (FIG. 15D). Additionally, RIP could be immunoprecipitated through Sam68 from MEF cells following TNF stimulation, indicating that these proteins associate in a TNF-induced signaling complex (FIG. 15E).

Immunoblotting was performed to test whether Sam68 is phosphorylated by TNF during the signaling process. To analyze whether TNF induces tyrosine phosphorylation of Sam68, antibodies that detect phospho-tyrosine were used. No enhancement in phosphorylation of tyrosine residues on Sam68 was detected following TNF stimulation.

To analyze whether TNF induces serine or threonine phosphorylation of Sam68, an in vivo orthophosphate-labeling assay was performed: Following starvation of cells for 90 min in phosphate-free medium with 10% dialyzed serum (Sigma), [$^{32}$P] orthophosphate (PerkinElmer NEN Radiochemicals) (0.1 mCi/ml) was added for an additional 90-min period. Cells were treated with TNF and harvested, washed with phosphate-free medium, and lysed in kinase lysis buffer (Ramakrishnan et al., 2004. Immunity 21, 477-489.). Sam68 was immunoprecipitated, immunoblotted and phosphate incorporation was assessed by autoradiography. It was observed that incubation of starved cells with serum increased tyrosine phosphorylation on Sam68 (FIG. 11A).

Although TNF-induced degradation of IκBα was seen as an indication of effective TNF signaling, no radio-phosphate incorporation in Sam68 could be detected following TNF stimulation. (FIG. 11B).

Sam68 is Part of Complex II of TNF Receptor Signaling and it is Required for RIP Recruitment and Apoptosis The composition of the FADD-caspase8-containing cytoplasmic complex II was analyzed in wild type and Sam68 knockout cells. Endogenous immunoprecipitation of FADD was performed using the same protocol as the endogenous Sam68 immunoprecipitation described above. Antibody against FADD was obtained from Santa Cruz Biotechnology, and antibody against Caspase8 was obtained from Enzo Life Sciences. In wild-type cells, long time TNF stimulation resulted in FADD-caspase8 association and this complex also contained RIP (FIG. 12A left panel). In Sam68 knockout cells, RIP binding to complex II was completely blocked. Moreover, Sam68 knockout cells also showed very high constitutive binding of caspase8 with FADD (FIG. 12A right panel). This abundant FADD-Capsase8 complex was inactive as it failed to induce any capsase3 activation or PARP cleavage in Sam68 knockout cells (FIG. 12B).

Figure 12:
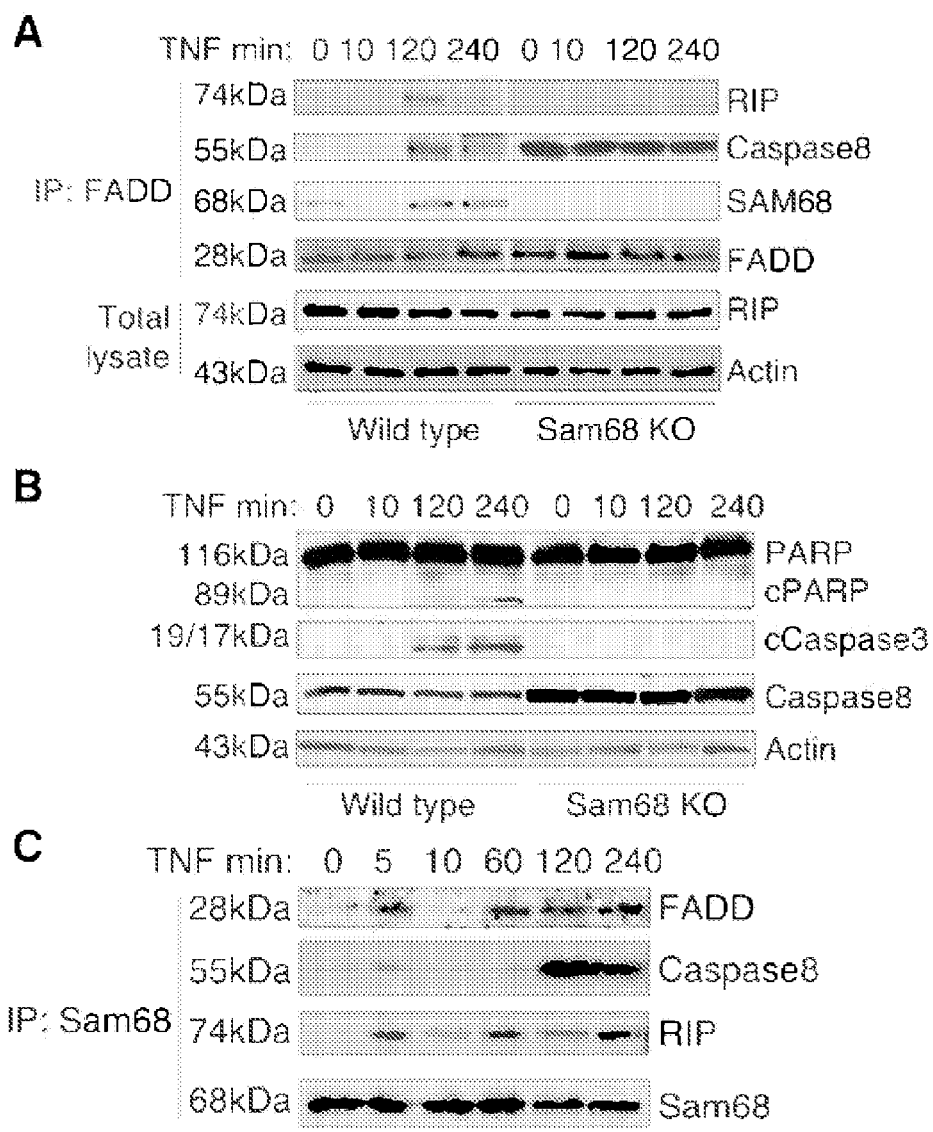
FIG. 12 illustrates Sam68 is required for signaling from complex II of TNF receptor. (A-C) Sam68 is associated with the late complex II formed after TNFR stimulation.

Immunoprecipitation of complex II components from wild type fibroblast cell extracts was performed through Sam68 using the endogenous Sam68 immunoprecipitation protocol described above. Following prolonged TNF stimulation, the complex containing caspase8, FADD and RIP was immunoprecipitated through Sam68 (FIG. 12C). An early, relatively weak association between FADD and caspase8 with Sam68 was observed at 5 minutes following TNF stimulation. This association decreased at 10 minutes, and later appeared as part of complex II (FIG. 12C). Caspase8 appeared in the complex after FADD recruitment occurred (FIG. 12C). RIP was found to be associated with Sam68, though with some modulation in its levels throughout the TNF stimulation period (FIG. 12).

Sam68 Deficiency Increases the mRNA Levels, but not the Activity of A20:

Sam68 knockout cells showed an increase in the mRNA level of A20. A20 has been suggested to modulate RIP ubiquitylation and levels (Vallabhapurapu and Karin, 2009). Wild-type and Sam68 knockout fibroblasts were analyzed for A20 protein levels using immunoblotting (A20 antibody was obtained from Santa Cruz Biotechnology). Though A20 protein level was increased in Sam68 knockout cells (FIG. 13A), these cells did not exhibit an increase in the amount of A20 recruited to the TNFR (FIG. 13B). Moreover, partial suppression of A20 by siRNA did not enhance TNF-induced RIP ubiquitylation in Sam68 knockout cells (FIGS. 13C and 13D).

What is claimed is:

1. A method of modulating TNF-dependent cytokine receptor signaling in a cell, the method comprising:
   administering an inhibitor of Sam68 to the cell, and
   monitoring at least one marker of TNF-dependent signaling in the cell.

2. The method of claim 1, wherein the cytokine receptor signaling is TNF-dependent NF-kB signaling.

3. The method of claim 1, wherein the cytokine receptor signaling is TNF-dependent signaling via an extrinsic apoptosis pathway.

4. The method of claim 1 wherein the Sam68 inhibitor is siRNA against Sam68.

5. The method of claim 1, wherein the Sam68 inhibitor is shRNA against Sam68.

6. The method of claim 1, wherein the Sam68 inhibitor is an anti-Sam68 antibody.

7. The method of claim 1, wherein the at least one marker of TNF-dependent signaling is selected from the group consisting of: ubiquitylated RIP, association of TRAF2 with TNFR, phosphorylation of IKK1, phosphorylation of IKK2, phosphorylation of NEMO, ubiquitylation of RIP, ubiquitylation of at least one IκB protein, IκBα degradation, translocation of at least one NF-κB family transcription factors into the nucleus, and expression of at least one NF-κB target gene.

8. The method of claim 1, wherein the at least one marker of TNF-dependent signaling is selected from the group consisting of: cleaved PARP, cleaved Caspase 3, cleaved Caspase 8 trypan blue exclusion of dead cells, neutral red assay, TUNEL staining, and association of RIP with FADD.

9. The method of claim 1, wherein administering an inhibitor of Sam68 eliminates substantially all Sam68 expression or activity.

10. The method of claim 1, wherein administering an inhibitor of Sam68 reduces, but does not eliminate Sam68 expression or activity.

11. A method of treating a disease or disorder associated with TNF-dependent signaling, the method comprising:
inhibiting TNF-dependent signaling by administering a therapeutically effective amount of Sam68 inhibitor to a patient identified to be in need of such treatment, thereby treating the disease or disorder associated with TNF-dependent signaling.

12. The method of claim 11, the method further comprising monitoring markers of TNF-dependent signaling.

13. The method of claim 11 or 12, wherein the TNF-dependent signaling is NF-kB signaling.

14. The method of claim 11 or 12, wherein the TNF-dependent signaling is via an extrinsic apoptosis pathway.

15. The method of claim 11, wherein the Sam68 inhibitor is a siRNA against Sam68.

16. The method of claim 11, wherein the Sam68 inhibitor is a shRNA against Sam68.

17. The method of claim 11, wherein the Sam68 inhibitor is a an anti-Sam68 antibody.

18. A method of disrupting a TNF signaling complex in a mammalian cell, the method comprising:
providing a mammalian cell;
administering an inhibitor of Sam68 to the cell; and
monitoring at least one marker of integrity or activity of the TNF signaling complex, thereby disrupting the TNF signaling complex in the mammalian cell.

19. The method of claim 18, wherein the TNF signaling complex is complex I or complex II.

20. The method of claim 18, wherein the at least one marker is selected from the group consisting of: ubiquitylated RIP, association of TRAF2 with TNFR, and association of RIP with FADD.

* * * * *

SEQUENCE LISTING

<160> NUMBER OF SEQ ID NOS: 45

<210> SEQ ID NO 1
<211> LENGTH: 19
<212> TYPE: DNA
<213> ORGANISM: Artificial Sequence
<220> FEATURE:
<223> OTHER INFORMATION: Mouse A20 Forward  PRIMER 5'

<400> SEQUENCE: 1
gaacagcgat caggccagg                                                    19

<210> SEQ ID NO 2
<211> LENGTH: 22
<212> TYPE: DNA
<213> ORGANISM: Artificial Sequence
<220> FEATURE:
<223> OTHER INFORMATION: Mouse A20 Reverse PRIMER 3'

<400> SEQUENCE: 2
ggacagttgg gtgtctcaca tt                                                22

<210> SEQ ID NO 3
<211> LENGTH: 20
<212> TYPE: DNA
<213> ORGANISM: Artificial Sequence
<220> FEATURE:
<223> OTHER INFORMATION: Mouse CCL-5 FORWARD  PRIMER 5'

<400> SEQUENCE: 3
gctgctttgc ctacctctcc                                                   20

<210> SEQ ID NO 4
<211> LENGTH: 21
<212> TYPE: DNA
<213> ORGANISM: Artificial Sequence
<220> FEATURE:
<223> OTHER INFORMATION: Mouse CCL-5 Reverse PRIMER 3'

<400> SEQUENCE: 4
tcgagtgaca aacacgactg c                                                 21

<210> SEQ ID NO 5
<211> LENGTH: 19
<212> TYPE: DNA
<213> ORGANISM: Artificial Sequence
<220> FEATURE:
<223> OTHER INFORMATION: Mouse c-Fos FORWARD  PRIMER 5'

<400> SEQUENCE: 5
cccatcctta cggactccc                                                    19

<210> SEQ ID NO 6
<211> LENGTH: 22
<212> TYPE: DNA
<213> ORGANISM: Artificial Sequence
<220> FEATURE:
<223> OTHER INFORMATION: Mouse c-Fos Reverse PRIMER 3'

<400> SEQUENCE: 6
gagatagctg ctctactttg cc                                                22

<210> SEQ ID NO 7
<211> LENGTH: 21
<212> TYPE: DNA

<213> ORGANISM: Artificial Sequence
<220> FEATURE:
<223> OTHER INFORMATION: Mouse cIAP2 FORWARD PRIMER 5'

<400> SEQUENCE: 7
acgcagcaat cgtgcattt g                                              21

<210> SEQ ID NO 8
<211> LENGTH: 22
<212> TYPE: DNA
<213> ORGANISM: Artificial Sequence
<220> FEATURE:
<223> OTHER INFORMATION: Mouse cIAP2 Reverse PRIMER 3'

<400> SEQUENCE: 8
cctataacga ggtcactgac gg                                            22

<210> SEQ ID NO 9
<211> LENGTH: 20
<212> TYPE: DNA
<213> ORGANISM: Artificial Sequence
<220> FEATURE:
<223> OTHER INFORMATION: Mouse I B  FORWARD  PRIMER 5'

<400> SEQUENCE: 9
ctgcaggcca ccaactacaa                                               20

<210> SEQ ID NO 10
<211> LENGTH: 21
<212> TYPE: DNA
<213> ORGANISM: Artificial Sequence
<220> FEATURE:
<223> OTHER INFORMATION: Mouse I B  Reverse PRIMER 3'

<400> SEQUENCE: 10
cagcacccaa agtcaccaag t                                             21

<210> SEQ ID NO 11
<211> LENGTH: 20
<212> TYPE: DNA
<213> ORGANISM: Artificial Sequence
<220> FEATURE:
<223> OTHER INFORMATION: Mouse ICAM1 FORWARD  PRIMER 5'

<400> SEQUENCE: 11
ttcacactga atgccagctc                                               20

<210> SEQ ID NO 12
<211> LENGTH: 20
<212> TYPE: DNA
<213> ORGANISM: Artificial Sequence
<220> FEATURE:
<223> OTHER INFORMATION: Mouse ICAM1 Reverse PRIMER 3'

<400> SEQUENCE: 12
gtctgctgag accctctttg                                               20

<210> SEQ ID NO 13
<211> LENGTH: 17
<212> TYPE: DNA
<213> ORGANISM: Artificial Sequence
<220> FEATURE:
<223> OTHER INFORMATION: Mouse IP10 FORWARD  PRIMER 5'

<400> SEQUENCE: 13
aggacggtcc gctgcaa                                                  17

-continued

```
<210> SEQ ID NO 14
<211> LENGTH: 20
<212> TYPE: DNA
<213> ORGANISM: Artificial Sequence
<220> FEATURE:
<223> OTHER INFORMATION: Mouse IP10 Reverse PRIMER 3'

<400> SEQUENCE: 14
cattctcact ggcccgtcat                                                 20

<210> SEQ ID NO 15
<211> LENGTH: 19
<212> TYPE: DNA
<213> ORGANISM: Artificial Sequence
<220> FEATURE:
<223> OTHER INFORMATION: Mouse L32 FORWARD  PRIMER 5'

<400> SEQUENCE: 15
aagcgaaact ggcggaaac                                                  19

<210> SEQ ID NO 16
<211> LENGTH: 20
<212> TYPE: DNA
<213> ORGANISM: Artificial Sequence
<220> FEATURE:
<223> OTHER INFORMATION: Mouse L32 Reverse PRIMER 3'

<400> SEQUENCE: 16
taaccgatgt tgggcatcag                                                 20

<210> SEQ ID NO 17
<211> LENGTH: 20
<212> TYPE: DNA
<213> ORGANISM: Artificial Sequence
<220> FEATURE:
<223> OTHER INFORMATION: Mouse MCP-1 FORWARD  PRIMER 5'

<400> SEQUENCE: 17
ctgaagacct tagggcagat                                                 20

<210> SEQ ID NO 18
<211> LENGTH: 21
<212> TYPE: DNA
<213> ORGANISM: Artificial Sequence
<220> FEATURE:
<223> OTHER INFORMATION: Mouse MCP-1 Reverse PRIMER 3'

<400> SEQUENCE: 18
aaggaatggg tccagacata c                                               21

<210> SEQ ID NO 19
<211> LENGTH: 23
<212> TYPE: DNA
<213> ORGANISM: Artificial Sequence
<220> FEATURE:
<223> OTHER INFORMATION: Mouse TNF  FORWARD  PRIMER 5'

<400> SEQUENCE: 19
tgccatcatt ctttgcatct tga                                             23

<210> SEQ ID NO 20
<211> LENGTH: 23
<212> TYPE: DNA
<213> ORGANISM: Artificial Sequence
<220> FEATURE:
<223> OTHER INFORMATION: Mouse TNF  Reverse PRIMER 3'
```

```
<400> SEQUENCE: 20
tgccatcatt ctttgcatct tga                                              23

<210> SEQ ID NO 21
<211> LENGTH: 21
<212> TYPE: DNA
<213> ORGANISM: Artificial Sequence
<220> FEATURE:
<223> OTHER INFORMATION: Mouse TNF  FORWARD  PRIMER 5'

<400> SEQUENCE: 21
gcagagagga ggttgacttt c                                                21

<210> SEQ ID NO 22
<211> LENGTH: 21
<212> TYPE: DNA
<213> ORGANISM: Artificial Sequence
<220> FEATURE:
<223> OTHER INFORMATION: Mouse TNF  Reverse PRIMER 3'

<400> SEQUENCE: 22
gcagagagga ggttgacttt c                                                21

<210> SEQ ID NO 23
<211> LENGTH: 21
<212> TYPE: DNA
<213> ORGANISM: Artificial Sequence
<220> FEATURE:
<223> OTHER INFORMATION: Mouse VCAM-1 FORWARD  PRIMER 5'

<400> SEQUENCE: 23
ccaaatccac gcttgtgttg a                                                21

<210> SEQ ID NO 24
<211> LENGTH: 21
<212> TYPE: DNA
<213> ORGANISM: Artificial Sequence
<220> FEATURE:
<223> OTHER INFORMATION: Mouse VCAM-1 Reverse PRIMER 3'

<400> SEQUENCE: 24
ggaatgagta gacctccacc t                                                21

<210> SEQ ID NO 25
<211> LENGTH: 18
<212> TYPE: DNA
<213> ORGANISM: Artificial Sequence
<220> FEATURE:
<223> OTHER INFORMATION: Human IP-10 FORWARD  PRIMER 5'

<400> SEQUENCE: 25
ctgactctaa gtggcatt                                                    18

<210> SEQ ID NO 26
<211> LENGTH: 18
<212> TYPE: DNA
<213> ORGANISM: Artificial Sequence
<220> FEATURE:
<223> OTHER INFORMATION: Human IP-10 Reverse PRIMER 3'

<400> SEQUENCE: 26
tgatggcctt cgattctg                                                    18

<210> SEQ ID NO 27
<211> LENGTH: 21
<212> TYPE: DNA
```

```
<213> ORGANISM: Artificial Sequence
<220> FEATURE:
<223> OTHER INFORMATION: Human TNF  FORWARD  PRIMER 5'

<400> SEQUENCE: 27
gcccaggcag tcagatcatc t                                              21

<210> SEQ ID NO 28
<211> LENGTH: 22
<212> TYPE: DNA
<213> ORGANISM: Artificial Sequence
<220> FEATURE:
<223> OTHER INFORMATION: Human TNF  Reverse PRIMER 3'

<400> SEQUENCE: 28
ttgagggttt gctacaacat gg                                             22

<210> SEQ ID NO 29
<211> LENGTH: 20
<212> TYPE: DNA
<213> ORGANISM: Artificial Sequence
<220> FEATURE:
<223> OTHER INFORMATION: Human VCAM-1 FORWARD  PRIMER 5'

<400> SEQUENCE: 29
tgttgagatc tcccctggac                                                20

<210> SEQ ID NO 30
<211> LENGTH: 20
<212> TYPE: DNA
<213> ORGANISM: Artificial Sequence
<220> FEATURE:
<223> OTHER INFORMATION: Human VCAM-1 Reverse PRIMER 3'

<400> SEQUENCE: 30
cgctcagagg gctgtctatc                                                20

<210> SEQ ID NO 31
<211> LENGTH: 21
<212> TYPE: DNA
<213> ORGANISM: Artificial Sequence
<220> FEATURE:
<223> OTHER INFORMATION: Human L32 FORWARD  PRIMER 5'

<400> SEQUENCE: 31
agctcccaaa aatagacgca c                                              21

<210> SEQ ID NO 32
<211> LENGTH: 22
<212> TYPE: DNA
<213> ORGANISM: Artificial Sequence
<220> FEATURE:
<223> OTHER INFORMATION: Human L32 Reverse PRIMER 3'

<400> SEQUENCE: 32
ttcatagcag taggcacaaa gg                                             22

<210> SEQ ID NO 33
<211> LENGTH: 57
<212> TYPE: DNA
<213> ORGANISM: Artificial Sequence
<220> FEATURE:
<223> OTHER INFORMATION: Sam68 shRNA (A) hairpin sequence

<400> SEQUENCE: 33
gatccgaaga ttcttggacc acaattcaag agattgtggt ccaagaatct tcttttt      57
```

-continued

```
<210> SEQ ID NO 34
<211> LENGTH: 21
<212> TYPE: DNA
<213> ORGANISM: Artificial Sequence
<220> FEATURE:
<223> OTHER INFORMATION: Sense siRNA (A) against Sam68

<400> SEQUENCE: 34
gaagauucuu ggaccacaat t                                              21

<210> SEQ ID NO 35
<211> LENGTH: 21
<212> TYPE: DNA
<213> ORGANISM: Artificial Sequence
<220> FEATURE:
<223> OTHER INFORMATION: Antisense siRNA (A) against Sam68

<400> SEQUENCE: 35
uuguggucca agaaucuuct t                                              21

<210> SEQ ID NO 36
<211> LENGTH: 57
<212> TYPE: DNA
<213> ORGANISM: Artificial Sequence
<220> FEATURE:
<223> OTHER INFORMATION: Sam68 shRNA (B) hairpin sequence

<400> SEQUENCE: 36
gatccccatg gaggaagtca agaattcaag agattcttga cttcctccat ggttttt       57

<210> SEQ ID NO 37
<211> LENGTH: 21
<212> TYPE: DNA
<213> ORGANISM: Artificial Sequence
<220> FEATURE:
<223> OTHER INFORMATION: Sense siRNA (B) against Sam68

<400> SEQUENCE: 37
ccauggagga agucaagaat t                                              21

<210> SEQ ID NO 38
<211> LENGTH: 21
<212> TYPE: DNA
<213> ORGANISM: Artificial Sequence
<220> FEATURE:
<223> OTHER INFORMATION: Antisense siRNA (B) against Sam68

<400> SEQUENCE: 38
uucuugacuu ccuccauggt t                                              21

<210> SEQ ID NO 39
<211> LENGTH: 57
<212> TYPE: DNA
<213> ORGANISM: Artificial Sequence
<220> FEATURE:
<223> OTHER INFORMATION: Sam68 shRNA (C) hairpin sequence

<400> SEQUENCE: 39
gatccgctta aaggttctga agtattcaag agatacttca gaacctttaa gcttttt       57

<210> SEQ ID NO 40
<211> LENGTH: 21
<212> TYPE: DNA
<213> ORGANISM: Artificial Sequence
<220> FEATURE:
<223> OTHER INFORMATION: Sense siRNA (C) against Sam68
```

```
<400> SEQUENCE: 40
gcuuaaaggu ucugaaguat t                                              21

<210> SEQ ID NO 41
<211> LENGTH: 21
<212> TYPE: DNA
<213> ORGANISM: Artificial Sequence
<220> FEATURE:
<223> OTHER INFORMATION: Antisense siRNA (C) against Sam68

<400> SEQUENCE: 41
uacuucagaa ccuuuaagct t                                              21

<210> SEQ ID NO 42
<211> LENGTH: 19
<212> TYPE: RNA
<213> ORGANISM: Artificial Sequence
<220> FEATURE:
<223> OTHER INFORMATION: siRNA #1 against mouse Sam68

<400> SEQUENCE: 42
gaaagaacgc gugcugaua                                                 19

<210> SEQ ID NO 43
<211> LENGTH: 19
<212> TYPE: RNA
<213> ORGANISM: Artificial Sequence
<220> FEATURE:
<223> OTHER INFORMATION: siRNA #2 against mouse Sam68

<400> SEQUENCE: 43
gaggagaauu auuuggauu                                                 19

<210> SEQ ID NO 44
<211> LENGTH: 19
<212> TYPE: RNA
<213> ORGANISM: Artificial Sequence
<220> FEATURE:
<223> OTHER INFORMATION: siRNA #3 against mouse Sam68

<400> SEQUENCE: 44
uaccagauau gauggauga                                                 19

<210> SEQ ID NO 45
<211> LENGTH: 19
<212> TYPE: RNA
<213> ORGANISM: Artificial Sequence
<220> FEATURE:
<223> OTHER INFORMATION: siRNA #4 against mouse Sam68

<400> SEQUENCE: 45
uuacgaagcc uacggacaa                                                 19
```